US012668616B2

(12) United States Patent
Weiner et al.

(10) Patent No.: US 12,668,616 B2
(45) Date of Patent: *Jun. 30, 2026

(54) WT1 VACCINE

(71) Applicants: The Trustees of the University of Pennsylvania, Philadelphia, PA (US); Inovio Pharmaceuticals, Inc., Plymouth Meeting, PA (US)

(72) Inventors: David B. Weiner, Merion, PA (US); Jian Yan, Wallingford, PA (US); Jewell Walters, Ramona, CA (US)

(73) Assignees: The Trustees of the University of Pennsylvania, Philadelphia, PA (US); Inovio Pharmaceuticals, Inc., Plymouth Meeting, PA (US)

( * ) Notice: Subject to any disclaimer, the term of this patent is extended or adjusted under 35 U.S.C. 154(b) by 80 days.

This patent is subject to a terminal disclaimer.

(21) Appl. No.: 18/162,104

(22) Filed: Jan. 31, 2023

(65) Prior Publication Data

US 2023/0293653 A1    Sep. 21, 2023

Related U.S. Application Data

(63) Continuation of application No. 16/221,707, filed on Dec. 17, 2018, now Pat. No. 11,638,747, which is a continuation of application No. 14/651,492, filed as application No. PCT/US2013/075141 on Dec. 13, 2013, now Pat. No. 10,220,082.

(60) Provisional application No. 61/737,094, filed on Dec. 13, 2012.

(51) Int. Cl.
*C07K 14/47* (2006.01)
*A61K 39/00* (2006.01)

(52) U.S. Cl.
CPC ...... *C07K 14/4748* (2013.01); *A61K 39/0011* (2013.01); *A61K 39/001153* (2018.08); *A61K 2039/53* (2013.01)

(58) Field of Classification Search
None
See application file for complete search history.

(56) References Cited

U.S. PATENT DOCUMENTS

| | | |
|---|---|---|
| 7,655,249 B2 | 2/2010 | Gaiger |
| 2003/0039635 A1 | 2/2003 | Gaiger |
| 2003/0198622 A1 | 10/2003 | Gaiger |
| 2003/0235557 A1 | 12/2003 | Gaiger |
| 2006/0216722 A1 | 9/2006 | Betsholtz |
| 2007/0037165 A1 | 2/2007 | Venter |
| 2010/0111986 A1 | 5/2010 | Scheinberg |
| 2010/0292160 A1 | 11/2010 | Sugiyama |
| 2011/0070251 A1 | 3/2011 | Sugiyama |
| 2012/0014945 A1 | 1/2012 | Wu |
| 2012/0232133 A1 | 9/2012 | Balazs |
| 2012/0269723 A1 | 10/2012 | Brinkmann |
| 2013/0177573 A1 | 7/2013 | Williamson |
| 2013/0243789 A1 | 9/2013 | Carson |

FOREIGN PATENT DOCUMENTS

| | | |
|---|---|---|
| CN | 1671733 | 9/2005 |
| EP | 2172476 | 4/2010 |
| JP | 2005518192 | 6/2005 |
| JP | 2007515393 | 6/2007 |
| KR | 20150130284 | 11/2015 |
| WO | 2011094358 A1 | 8/2011 |
| WO | 2012065164 A2 | 5/2012 |
| WO | 2012106377 A2 | 8/2012 |
| WO | WO 13/106834 * | 7/2013 |
| WO | 2014144885 | 9/2014 |

OTHER PUBLICATIONS

Makita et al., Clin. Cancer Res., 2002, 8: 2626-2631.*
Fujiki et al., Microbiol. Immunol., 2008, 52: 591-600.*
Sequence alignment, 2025.*
Sequence alignment, 2005.*
Database Uniprot Accession No. G3RQ97, Wilms tumor 1, Nov. 16, 2011, http://www.uniprot.org/uniprot/G3RQ97 (5 pages).
Database Uniprot Accession No. 10FUW6, Wilms tumor protein isoform A, Jun. 13, 2012, http://www.uniprot.org/uniprot/10FUW6 (5 pages).
Haber et al., "Alternative splicing and genomic structure of the Wilms tumor gene WT1", PNAS USA, Nov. 30, 1991, vol. 88, pp. 9618-9622.
Oka et al., "WT1 Peptide Vaccine for the treatment of cancer", Current Opinion in Immunology, May 24, 2008, vol. 2, pp. 211-220.
Tian et al., "Design and Construction of Multi-Epitope Fusion Gene Vaccine of Wilm Tumor Gene WT1 and Stimulating Epitope of Mycobacterium Tuberculosis Heat Shock Protein 70," Blood, 2010, 116, poster 4713.

* cited by examiner

*Primary Examiner* — Ileana Popa
(74) *Attorney, Agent, or Firm* — Riverside Law LLP

(57) ABSTRACT

Disclosed herein are nucleic acid molecules comprising one or more nucleic acid sequences that encode a mutated WT1 antigen. Vectors, compositions and vaccines comprising one or more nucleic acid sequences that encode a mutated WT1 antigen are disclosed. Methods of treating an individual who has a WT1-expressing tumor and methods of preventing a WT1-expressing tumor are disclosed. Mutated WT1 antigen is disclosed.

18 Claims, 11 Drawing Sheets

Specification includes a Sequence Listing.

75

50

ConWT1-L Nucleotide Sequence (SEQ ID NO:1)

FIG. 6A

ConWT1-L Amino Acid Sequence (SEQ ID NO:2)

FIG. 6B

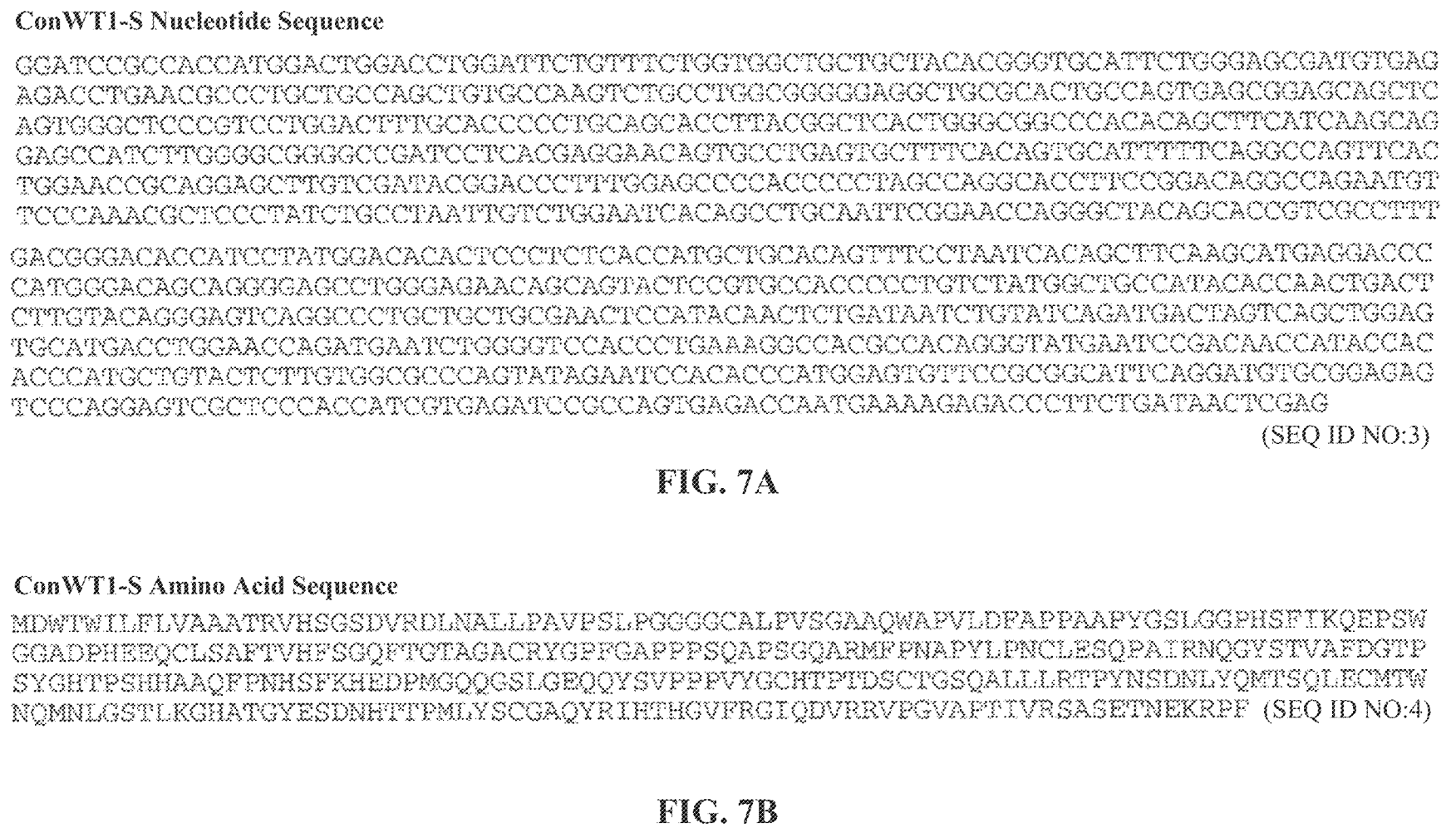

ConWT1-S Nucleotide Sequence

GGATCCGCCACCATGGACTGGACCTGGATTCTGTTTCTGGTGGCTGCATTCTGGGATGTGGAGAGACCTGAAGCGCCTGCAGTCTGCCAGTGCTGCAGGCTGGGCGGCGGAGCTGCACTGCCAGTGCGCCACTGCAGTGAGGCTGAGCAGGTCAGTGGCCTCCGTCCGGGCTTCTGACCTTTGCACCCCCTTACGCTGAGCAGCTCACTGGGCGGCTCCACCTTACGCTGAGCAGCTTCATCAAGCAGGAGCCATCTGGGCGGCGGGCCGATCCTCACGAGGAACAGTGCTTGAGTGTCAGGCATTTTCAGGCAGTTCACTGGAACCGCAGGAGCTTGTGTGATAACGGACCCTTTGGAGCCCCCAGCCCTTCCGGACAGCCCAGAATGTTCCCAAAGCTTCCCTATCTGCCTAATTGTCTGTGGAATCACAGGGCTACAGGGCTACACGGCTGCTTT (SEQ ID NO:3)

GACGGGACACCATCTATGGACAATCTGACACACCCCTCTCACACATGCTGGACAGTTTCCTAATCACAGCTTCAGCATGAGGACACCCCATGCCGACAGCAGCGGCAGCCGGACTCCGGTGCCCTCCCAGCCATACAGCCAACTGACTCTTGTACAGGGAGTCAGGCCCTGCTCGAACTCCAATACAACTGTGATAATGACTCCATAGATGACTAGCTGGAGTGCATGACCTGGAACCAGATGAATCTGGGGTTCCACCCTGAAAGCCCACGGTTATGAATCCGACAACCATACCACACCCATGCTGTACTCTTGTGGCGCCCAGTATAGAATCCACACCATGGATGTCCGGGATTCAGGATGTGCGGGAGAGTCCCAGGAGTCGGTCCCCACCATCGGCCCAGTGAGACATCGGCCAATGAAAAGAGACCCTTCTGATAACTCGAG (SEQ ID NO:3)

FIG. 7A

ConWT1-S Amino Acid Sequence

MDWTWILFLVAAATRVHSGSDVRDLNALLPAVPSLPGGGGCALPVSGAAQWAPVLDPAPPAAPYGSLGGPHSFIKQEPSWGGADPHEEQCLSAFTVHFSGQFTQTAGACRYGPFGAPPSQASGQARMFPNAPYLPNCLESQPAIRNQGYSTVAFDGTPSYGHTPSHHAAQFPNHSFKHEDPMGQQGSLGEQQYSVPPPVYGCHTPTDSCTGSQALLRTPYNSDNLYQMTSQLECMTWNQMNLGSTLKGHATGYESDNHTTPMIYSCGAQYRIHTHGVFRGIQDVRRVPGVAFTIVRSASETNEKRPF (SEQ ID NO:4)

FIG. 7B

WT1 VACCINE

CROSS REFERENCE TO RELATED APPLICATION

The present application is a continuation of U.S. patent application Ser. No. 14/651,492, filed Jun. 11, 2015, which is the U.S. national phase application filed under 35 U.S.C. § 371 claiming benefit to International Patent Application No. PCT/US2013/075141, filed Dec. 13, 2013, which is entitled to priority under 35 U.S.C § 119(e) to U.S. Provisional Patent Application No. 61/737,094, filed Dec. 13, 2012, each of which applications are incorporated by reference herein in their entireties.

REFERENCE TO SEQUENCE LISTING SUBMITTED ELECTRONICALLY

This application contains a sequence listing, which is submitted electronically via Patent Center as an XML, formatted sequence listing with a file name "206108_0026_02US_SequenceListing.xml", created on Jan. 29, 2023, file size of 10,876 bytes. Except for changes to the xml format, bibliographic information, this Sequence Listing is identical to an ASCII formatted sequence listing with a file name "206108_0026_01US_ 608353_SequenceListing.txt" and "206108_0026_ 00US_604320_seqlisting.txt". The sequence listing submitted via Patent Center is part of the specification and is herein incorporated by reference in its entirety.

TECHNICAL FIELD

The present invention relates to Wilm's tumor (WT1) immunogens and nucleic acid molecules which encode the same. The present invention also relates to vaccines including such WT1 immunogens and/or nucleic acid molecules. The present invention further relates to methods of using the vaccines for inducing immune responses and preventing and/or treating subjects having tumors that express WT1.

BACKGROUND

Cancer remains a major cause of death in the U.S. and worldwide. The cancer vaccine market is growing rapidly. Lymphoma vaccines account for about 0.5% of the market. Effective tumor vaccines may be useful to prevent tumor growth and/or may be useful as being a more effective, less toxic alternative to standard treatments for patients with advanced cancers. An antigen associated with cancer and therefore, a target for anti-tumor vaccines is WT1.

Wilm's tumor suppressor gene 1 (WT1) was identified as a cause of an embryonic malignancy of the kidney, affecting around 1 in 10,000 infants. It occurs in both sporadic and hereditary forms. Inactivation of WT1 leads to the development of Wilm's tumour, and Denys-Drash syndrome (DDS). The result is both a nephropathy as well as possible genital abnormalities. The WT1 protein has been found to interact with a host of cellular factors, including the major tumor regulator gene p53, which is also a tumor suppressor transcription factor.

WT1 is expressed in many tumor types and has been more broadly implicated in many cancers. For example, WT1 protein is localized in the cell nuclei of 75% of mesotheliomas (14,200 cases annually worldwide, with the highest incidence in the US) and in 93% of ovarian serous carcinomas (190,000 ovarian cancer cases worldwide in 2010).

Additionally, WT1 has been implicated in pancreatic cancers, leukemia, lung cancer, breast cancer, colon cancer, glioblastoma, head and neck cancer as well as in benign mesothelium and cervical and ovarian cancer among others. WT1 is a target for gene therapy or immune therapy as an approach to cancer treatment.

WT1 encodes a transcription factor that contains four zinc finger motifs at the C-terminus and a proline/glutamine-rich DNA-binding domain at the N-terminus. It has an essential role in the normal development of the urogenital system. It is, however, more dispensable in adults, thus suggesting it as a target for immune therapy. Multiple transcript variants, resulting from alternative splicing at two coding exons, have been well characterized. Use of the entire reading frame to maximize CTL coverage would be considered an advantage.

Due to the conservation of the WT1 antigen, most attempts to generate strong immunity against this gene target have not been successful. Vaccines have been previously investigated using DNA vaccine technology, pox-viral vaccine technology, Adenoviral vaccine technology, peptide vaccine technology and protein based vaccine technology. The vaccines that were investigated used the true, gene structure i.e., the native, "normal" gene. Only low level or nonfunctional T cell immunity was achieved in these investigations.

There are a few major issues with development of a more effective WT1 immunogen. Due to the similarity of the WT1 antigen to host WT1, a strong suppressor T cell response is generated, thereby blocking immune induction. In addition, the gene itself is significantly processed at the RNA level so that multiple cleaved transcripts are generated of unknown and possibly competing value. Furthermore, expression of the delivered WT1 is low, resulting in poor immunity.

Vaccines for the treatment and prevention of cancer are of great interest. Existing vaccines targeting WT1 are limited by poor antigen expression in vivo. Accordingly, a need remains in the art for the development of safe and effective vaccines that are applicable to tumors expressing WT1, thereby providing treatment of and promoting survival of such cancers.

SUMMARY

The present invention is directed to an isolated nucleic acid molecule comprising one or more nucleic acid sequences selected from the group consisting of: a nucleic acid sequence that encodes SEQ ID NO:2, a nucleic acid sequence that encodes a fragment comprising at least 90% of a length of SEQ ID NO:2, a nucleic acid sequence that encodes a protein that is at least 98% identical to SEQ ID NO:2, a nucleic acid sequence that encodes a fragment comprising at least 90% of a length of a protein that is at least 98% identical to SEQ ID NO:2, a nucleic acid sequence that encodes SEQ ID NO:4, a nucleic acid sequence that encodes a fragment comprising at least 90% of a length of SEQ ID NO:4, a nucleic acid sequence that encodes a protein that is at least 98% identical to SEQ ID NO:4, and a nucleic acid sequence that encodes a fragment comprising at least 90% of a length of a protein that is at least 98% identical to SEQ ID NO:4.

The present invention is also directed to an isolated nucleic acid molecule comprising one or more nucleic acid sequences selected from the group consisting of: SEQ ID NO: 1, a fragment comprising at least 90% of a length of SEQ ID NO:1, a nucleic acid sequence that is at least 98% identical to SEQ ID NO:1, a fragment comprising at least 90% of a length of a nucleic acid sequence that is at least 98% identical to SEQ ID NO:1, SEQ ID NO: 3, a fragment comprising at least 90% of a length of SEQ ID NO:3, a nucleic acid sequence that is at least 98% identical to SEQ ID NO:3, and a fragment comprising at least 90% of a length of a nucleic acid sequence that is at least 98% identical to SEQ ID NO:3.

The above nucleic acid molecule can be incorporated into a plasmid or a viral vector. The present invention is further directed to a composition comprising one or more of the above nucleic acid molecules. The present invention is also directed to a vaccine comprising one or more of the above nucleic acid molecules.

The present invention is further directed to a method of treating an individual who has a WT1-expressing tumor comprising administering an amount of the above vaccine effective to slow growth of, reduce or eliminate WT1-expressing tumors.

The present invention is also directed to a method of preventing a WT1-expressing tumor in an individual comprising administering an amount of the above vaccine effective to inhibit formation or growth of WT1-expressing tumors.

The present invention is further directed to a protein comprising the amino acid sequence selected from the group consisting of: SEQ ID NO:2, a fragment comprising at least 90% of a length of SEQ ID NO:2, an amino acid sequence that is at least 98% identical to SEQ ID NO:2, a fragment comprising at least 90% of a length of an amino acid sequence that is at least 98% identical to SEQ ID NO:2, SEQ ID NO:4, a fragment comprising at least 90% of a length of SEQ ID NO:4, an amino acid sequence that is at least 98% identical to SEQ ID NO:4, and a fragment comprising at least 90% of a length of an amino acid sequence that is at least 98% identical to SEQ ID NO:4.

The present invention is also directed to a vaccine comprising a nucleic acid molecule. The nucleic acid molecule can comprise a nucleic acid sequence having at least about 90% identity over an entire length of the nucleic acid sequence set forth in SEQ ID NO:1. The nucleic acid molecule can comprise a nucleic acid sequence having at least about 90% identity over an entire length of the nucleic acid sequence set forth in SEQ ID NO:3. The vaccine can further comprise a peptide. The peptide can comprise an amino acid sequence having at least about 90% identity over an entire length of the amino acid sequence set forth in SEQ ID NO:2. The peptide can comprise an amino acid sequence having at least about 90% identity over an entire length of the amino acid sequence set forth in SEQ ID NO:4.

The nucleic acid molecule can comprise an expression vector. The vaccine can further comprise a pharmaceutically acceptable excipient. The vaccine can further comprise an adjuvant.

The present invention is also directed to a vaccine comprising a nucleic acid molecule. The nucleic acid molecule can encode a peptide comprising an amino acid sequence having at least about 90% identity over an entire length of the amino acid sequence set forth in SEQ ID NO:2. The nucleic acid molecule can encode a peptide comprising an amino acid sequence having at least about 90% identity over an entire length of the amino acid sequence set forth in SEQ ID NO:4. The vaccine can further comprise a peptide. The peptide can comprise an amino acid sequence having at least about 90% identity over an entire length of the amino acid sequence set forth in SEQ ID NO:2. The peptide can comprise an amino acid sequence having at least about 90% identity over an entire length of the amino acid sequence set forth in SEQ ID NO:4.

The nucleic acid molecule can comprise an expression vector. The vaccine can further comprise a pharmaceutically acceptable excipient. The vaccine can further comprise an adjuvant.

The present invention is further directed to a nucleic acid molecule comprising the nucleic acid sequence set forth in SEQ ID NO:1.

The present invention is also directed to a nucleic acid molecule comprising the nucleic acid sequence set forth in SEQ ID NO:3.

The present invention is further directed to a peptide comprising the amino acid sequence set forth in SEQ ID NO:2.

The present invention is also directed to a peptide comprising the amino acid sequence set forth in SEQ ID NO:4.

The present invention is further directed to a vaccine comprising an antigen, wherein the antigen is encoded by SEQ ID NO:1 or SEQ ID NO:3. The antigen can be encoded by SEQ ID NO:1. The antigen can be encoded by SEQ ID NO:3. The antigen can comprise the amino acid sequence set forth in SEQ ID NO:2 or SEQ ID NO:4. The antigen can comprise the amino acid sequence set forth in SEQ ID NO:2. The antigen can comprise the amino acid sequence set forth in SEQ ID NO:4.

The present invention is also directed to a vaccine comprising a peptide. The peptide can comprise an amino acid sequence having at least about 90% identity over an entire length of the amino acid sequence set forth in SEQ ID NO:2. The peptide can comprise an amino acid sequence having at least about 90% identity over an entire length of the amino acid sequence set forth in SEQ ID NO:4. The peptide can comprise the amino acid sequence set forth in SEQ ID NO:2. The peptide can comprise the amino acid sequence set forth in SEQ ID NO:4.

BRIEF DESCRIPTION OF THE DRAWINGS

FIG. 6A shows the nucleotide sequence encoding ConWT1-L; and FIG. 6B shows the amino acid sequence of ConWT1-L.

FIG. 7A shows the nucleotide sequence encoding ConWT1-S; and FIG. 7B shows the amino acid sequence of ConWT1-S.

DETAILED DESCRIPTION

Figure 1:
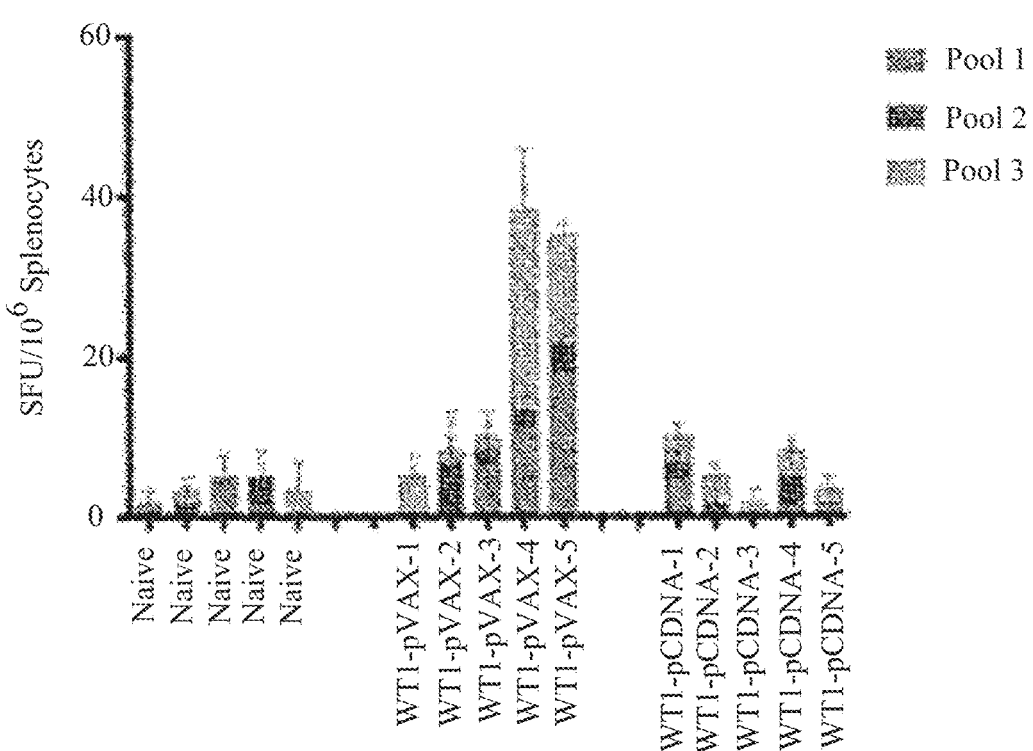
FIG. 1 shows a graph plotting immunization group vs. spot forming unit (SFU) per $10^6$ splenocytes

The present invention relates to a vaccine comprising a WT1 antigen. WT1 is expressed in many tumors. Accordingly, the vaccine provides treatment for a cancer or cancer-based tumor expressing WT1.

The WT1 antigen can be a consensus WT1 antigen derived from the sequences of WT1 from different species, and thus, the consensus WT1 antigen is unique. The consensus WT1 antigen is also unique in that the zinc fingers are modified or removed altogether. Modification can include substitution of the cysteine and histidine residues that coordinate zinc structure.

Surprisingly, when the consensus WT1 antigen has modified or no zinc fingers, a significant immune response is induced that is reactive to WT1. The induced immune response includes both humoral and cellular immune responses, in which the cellular immune response is induced by about 400-fold increase over or as compared to the cellular immune response induced by a vaccine comprising native WT1 or WT1 optimized for expression.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Adjuvant" as used herein may mean any molecule added to the DNA plasmid vaccines described herein to enhance antigenicity of the one or more antigens encoded by the DNA plasmids and encoding nucleic acid sequences described hereinafter.

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antigen" refers to: proteins having Mutated WT1 amino acid sequences including SEQ ID NO:2; fragments thereof of lengths set forth herein, variants, i.e. proteins with sequences having identity to SEQ ID NO:2 as set forth herein, fragments of variants having lengths set forth herein, SEQ ID NO:4; fragments thereof of lengths set forth herein, variants, i.e. proteins with sequences having identity to SEQ ID NO:4 as set forth herein, fragments of variants having lengths set forth herein, and combinations thereof. Antigens may optionally include signal peptides such as those from other proteins.

"Coding sequence" or "encoding nucleic acid" as used herein may refer to the nucleic acid (RNA or DNA molecule) that comprise a nucleotide sequence which encodes an antigen set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

"Consensus" or "Consensus Sequence" as used herein may mean a synthetic nucleic acid sequence, or corresponding polypeptide sequence, constructed based on analysis of an alignment of multiple subtypes of a particular antigen. The sequence may be used to induce broad immunity against multiple subtypes, serotypes, or strains of a particular antigen. Synthetic antigens, such as fusion proteins, may be manipulated to consensus sequences (or consensus antigens).

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antigen that is capable of eliciting an immune response in a mammal. A fragment of an antigen may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antigen, excluding any heterologous signal peptide added. The fragment may comprise a fragment of a polypeptide that is 95% or more, 96% or more, 97% or more, 98% or more or 99% or more identical to the antigen and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antigen.

A fragment of a nucleic acid sequence that encodes an antigen may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antigen and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more antigens described herein via the vaccines described herein. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Subject" as used herein can mean a mammal that wants to or is in need of being immunized with the herein described vaccine. The mammal can be a human, chimpanzee, dog, cat, horse, cow, mouse, or rat.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Treatment" or "treating," as used herein can mean protecting of an animal from a disease through means of preventing, suppressing, repressing, or completely eliminating the disease. Preventing the disease involves administering a vaccine of the present invention to an animal prior to onset of the disease. Suppressing the disease involves administering a vaccine of the present invention to an animal after induction of the disease but before its clinical appearance. Repressing the disease involves administering a vaccine of the present invention to an animal after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Vaccine

Provided herein are vaccines comprising an antigen, a fragment thereof, a variant thereof, or a combination thereof. The vaccines can be capable of generating in a mammal an immune response against the antigen. The vaccines may comprise a plasmid or a plurality of plasmids as described in more detail below. The vaccines can induce a therapeutic or prophylactic immune response.

The vaccines can be used to protect against cancer, for example, a cancer or tumor expressing Wilm's tumor suppressor gene 1 (WT1). The vaccines can be used to prevent and/or treat a tumor expressing WT1 in a subject in need thereof. The vaccines can induce cellular and/or antibody responses against WT1 and against tumors expressing WT1.

The vaccines can induce or elicit an immune response in the subject administered the vaccine. The immune response in the subject administered the vaccine can be induced by at least about 40-fold, 50-fold, 60-fold, 70-fold, 80-fold, 90-fold, 100-fold, 150-fold, 200-fold, 225-fold, 250-fold, 275-fold, 300-fold, 325-fold, 350-fold, 375-fold, 400-fold, 425-fold, 450-fold, 475-fold, 500-fold, 525-fold, 550-fold, 575-fold, 600-fold, 650-fold, 700-fold, 750-fold, 800-fold, 850-fold, 900-fold, 950-fold, 1000-fold, 1500-fold, 2000-fold, 2500-fold, 3000-fold, 3500-fold, or 4000-fold. In some embodiments, the immune response in the subject administered the vaccine can be induced by at least about 300-fold, 325-fold, 350-fold, 375-fold, 400-fold, 425-fold, 450-fold, 475-fold, or 500-fold.

The vaccines can induce a humoral and/or cellular immune response in the subject administered the vaccine. The induced humoral immune response can include antibodies that are immunoreactive to the antigen. The induced cellular immune response can include T cells that produce interferon-gamma (IFN-γ) and are immunoreactive with the antigen. The cellular immune response in the subject administered the vaccine can be induced by at least about 40-fold, 50-fold, 60-fold, 70-fold, 80-fold, 90-fold, 100-fold, 150-fold, 200-fold, 225-fold, 250-fold, 275-fold, 300-fold, 325-fold, 350-fold, 375-fold, 400-fold, 425-fold, 450-fold, 475-fold, 500-fold, 525-fold, 550-fold, 575-fold, 600-fold, 650-fold, 700-fold, 750-fold, 800-fold, 850-fold, 900-fold, 950-fold, 1000-fold, 1500-fold, 2000-fold, 2500-fold, 3000-fold, 3500-fold, or 4000-fold. In some embodiments, the cellular immune response in the subject administered the vaccine can be induced by at least about 300-fold, 325-fold, 350-fold, 375-fold, 400-fold, 425-fold, 450-fold, 475-fold, or 500-fold.

The vaccines can be used to deliver one or more antigens selected from the group consisting of: antigens, fragments of such antigens, variants of such antigens, and fragments of variants. In the case of delivery of multiple antigens, the vaccine may include multiple compositions or a single composition. Delivery can include a single plasmid which may be used to encode multiple different antigens or different portions of the same antigen. In other embodiments, delivery can include different plasmids that encode different antigens or different portions of the same antigen.

The vaccines can be a nucleic acid vaccine, a peptide vaccine, or a combination nucleic acid and peptide vaccine. The nucleic acid vaccine can comprise nucleic acid molecules. The nucleic acid vaccine can comprise a plurality of copies of a single nucleic acid molecule such as a single plasmid, a plurality of copies of a two or more different nucleic acid molecules such as two or more different plasmids.

The nucleic acid vaccine may comprise nucleic acid molecules, such as plasmids, that collectively contain coding sequence for a single antigen, heterologous coding sequence for two antigens or more. The nucleic acid vaccine comprising heterologous coding sequence of two antigens may be on a single nucleic acid molecule such as a single plasmid or the nucleic acid vaccine may comprise two different nucleic acid molecules such as two different plasmids, wherein one nucleic acid molecule comprises the heterologous coding sequence of one antigen and the other nucleic acid molecule comprises the heterologous coding sequence of a different antigen. The nucleic acid vaccine may comprise two different nucleic acid molecules such as two different plasmids, wherein one nucleic acid molecule comprises the heterologous coding sequence of a first portion of the antigen and the other nucleic acid molecule comprises the heterologous coding sequence of a second portion of the antigen.

Similarly, the nucleic acid vaccine comprising the heterologous coding sequence of three antigens may comprise a single nucleic acid molecule such as a single plasmid, two different nucleic acid molecules or three different nucleic acid molecules. Likewise, the nucleic acid vaccine comprising heterologous coding sequence of four antigens may comprise a single nucleic acid molecule such as a single plasmid, two different nucleic acid molecules, three different nucleic acid molecules or four different nucleic acid molecules.

The nucleic acid vaccine can include one or more nucleotide sequences encoding the antigen. The nucleic acid sequence can be DNA, RNA, cDNA, a variant thereof, a fragment thereof, or a combination thereof. The nucleic acid sequence can also include additional sequences that encode linker, leader, and/or tag sequences that are linked to the antigen by a peptide bond.

In some embodiments, the nucleic acid vaccine may further comprise coding sequence for a molecular adjuvant, in some cases the molecular adjuvant can be IL-12, IL-15, IL-28, IL-31, IL-33, and/or RANTES, and in some cases the molecular adjuvant is a checkpoint inhibitor, including anti-cytotoxic T-lymphocyte antigen 4 (CTLA-4), anti-programmed death receptor-1 (PD-1) and anti-lymphocyte-activation gene (LAG-3). Coding sequence for IL-12, IL-15, IL-28, IL-31, IL-33 and/or RANTES may be included on one or more nucleic acid molecules that comprise coding sequence for one or more antigens. Coding sequence for IL-12, IL-15, IL-28, IL-31, IL-33 and/or RANTES may be included on a separate nucleic acid molecules such as a separate plasmid.

The peptide vaccine can include an antigenic peptide, an antigenic protein, a variant thereof, a fragment thereof, or a combination thereof. The combination DNA and peptide vaccine can include the above described one or more nucleic acid sequences encoding the antigen and the antigenic peptide or antigenic protein.

The vaccine of the present invention can have features required of effective vaccines such as being safe so the vaccine itself does not cause illness or death; being protective against illness; inducing neutralizing antibody; inducing protective T cell; and providing ease of administration, few side effects, biological stability, and low cost per dose.

a. Antigen

As described above, the vaccine can comprise an antigen. The antigen can be Wilm's tumor suppressor gene 1 (WT1), a fragment thereof, a variant thereof, or a combination thereof. WT1 is a transcription factor containing at the N-terminus, a proline/glutamine-rich DNA-binding domain and at the C-terminus, four zinc finger motifs. WT1 plays a role in the normal development of the urogenital system and interacts with numerous factors, for example, p53, a known tumor suppressor and the serine protease HtrA2, which cleaves WT1 at multiple sites after treatment with a cytotoxic drug.

Mutation of WT1 can lead to tumor or cancer formation, for example, Wilm's tumor or tumors expressing WT1. Wilm's tumor often forms in one or both kidneys before metastasizing to other tissues, for example, but not limited to, liver tissue, urinary tract system tissue, lymph tissue, and lung tissue. Accordingly, Wilm's tumor can be considered a metastatic tumor. Wilm's tumor usually occurs in younger children (e.g., less than 5 years old) and in both sporadic and hereditary forms.

Accordingly, the vaccine can be used for treating subjects suffering from Wilm's tumor. The vaccine can also be used for treating subjects with cancers or tumors that express WT1 for preventing development of such tumors in subjects. The WT1 antigen can differ from the native, "normal" WT1 gene, and thus, provide therapy or prophylaxis against an WT1 antigen-expressing tumor. Accordingly, WT1 antigen sequences that differ from the native WT1 gene (i.e., mutated WT1 genes or sequences) are provided herein.

Transcripts of the native WT1 gene are processed into a variety of mRNAs, and the resulting proteins are not all of equal value for inducing an immune response. The mutated WT1 genes described herein avoid alternative processing, producing one full-length transcript and resulting in stronger induction of effector T and B cell responses. The first mutated WT1 sequence is referred to as CON WT1 with modified Zinc Fingers or ConWT1-L. SEQ ID NO: 1 is a nucleic acid sequence encoding the WT1 antigen CON WT1 with modified Zinc Fingers. SEQ ID NO:2 is the amino acid sequence of WT1 antigen CON WT1 with modified Zinc Fingers. The second mutated WT1 sequence is referred to as CON WT1 without Zinc Fingers or ConWT1-S. SEQ ID NO:3 is a nucleic acid sequence encoding the WT1 antigen CON WT1 without Zinc Fingers. SEQ ID NO:4 is the amino acid sequence of WT1 antigen CON WT1 without modified Zinc Fingers.

Isolated nucleic acid molecules comprising the above described heterologous sequences are provided. Isolated nucleic acid molecules consisting of the above described heterologous sequences are provided. Isolated nucleic acid molecules comprising the above described heterologous sequences may be incorporated into vectors such as plasmids, viral vectors and other forms of nucleic acid molecules as described below. Provided herein are nucleic acid sequences that encode WT1 antigens. Coding sequences encoding WT1 antigens have the sequences as described above.

Protein molecules comprising above described heterologous amino acid sequences are provided. Protein molecules consisting of above described heterologous amino acid sequences are provided. Provided herein are proteins and polypeptides having the above described sequences. The proteins and polypeptide may be referred to as WT1 antigens and WT1 immunogens. WT1 antigens are capable of eliciting an immune response against tumor expressing a WT1 antigen.

In one aspect of the invention, it is desired that the consensus antigen provides for improved transcription and translation, including having one or more of the following: low GC content leader sequence to increase transcription; mRNA stability and codon optimization and eliminating to the extent possible cis-acting sequence motifs (i.e., internal TAT A-boxes).

In some aspects of the invention, it is desired to generate a consensus antigen that generates a broad immune response across multiple strains, including having one or more of the following: incorporate all available full-length sequences; computer generated sequences that utilize the most commonly occurring amino acid at each position; and increase cross-reactivity between strains.

The WT1 antigen can be a consensus antigen (or immunogen) sequence derived from two or more species. The WT1 antigen can comprise a consensus sequence and/or modification(s) for improved expression. Modification can include codon optimization, RNA optimization, additional of a kozak sequence (e.g., GCC ACC) for increased translation initiation and/or the addition of an immunoglobulin leader sequence to increase the immunogenicity of the WT1 antigen. The WT1 antigen can comprise a signal peptide such as an immunoglobulin signal peptide, for example, but not limited to, an immunoglobulin E (IgE) or immunoglobulin G (IgG) signal peptide. In some embodiments, the WT1 consensus antigen can comprise a hemagglutinin (HA) tag. The WT1 consensus antigen can be designed to elicit stronger and broader cellular and/or humoral immune responses than a corresponding codon optimized WT1 antigen.

The WT1 consensus antigen can comprise one or more mutations in one or more zinc fingers, thereby eliciting stronger and broader cellular and/or humoral immune responses than a corresponding codon optimized WT1 antigen. The one or more mutations can be a substitution of one or more of the amino acids that coordinate the zinc ion in the one or more zinc fingers. The one or more amino acids that coordinate the zinc ion can be a CCHH motif. Accordingly, in some embodiments, the one or more mutations can replace 1, 2, 3, or all 4 amino acids of CCHH motif.

In other embodiments, the one or more mutations are such that residues 312, 317, 342, and 347 of SEQ ID NO:2 are any residue other than cysteine (C) and residues 330, 334, 360, and 364 of SEQ ID NO:2 are any residue other than histidine (H). In particular, the one or more mutations are such that residues 312, 317, 330, 334, 342, 347, 360, and 364 of SEQ ID NO:2 are glycine (G).

In other embodiments, one or more of the zinc fingers can be removed from the WT1 consensus antigen. One, two, three, or all four of the zinc fingers can be removed from the WT1 consensus antigen.

Figures 6A, 6B:
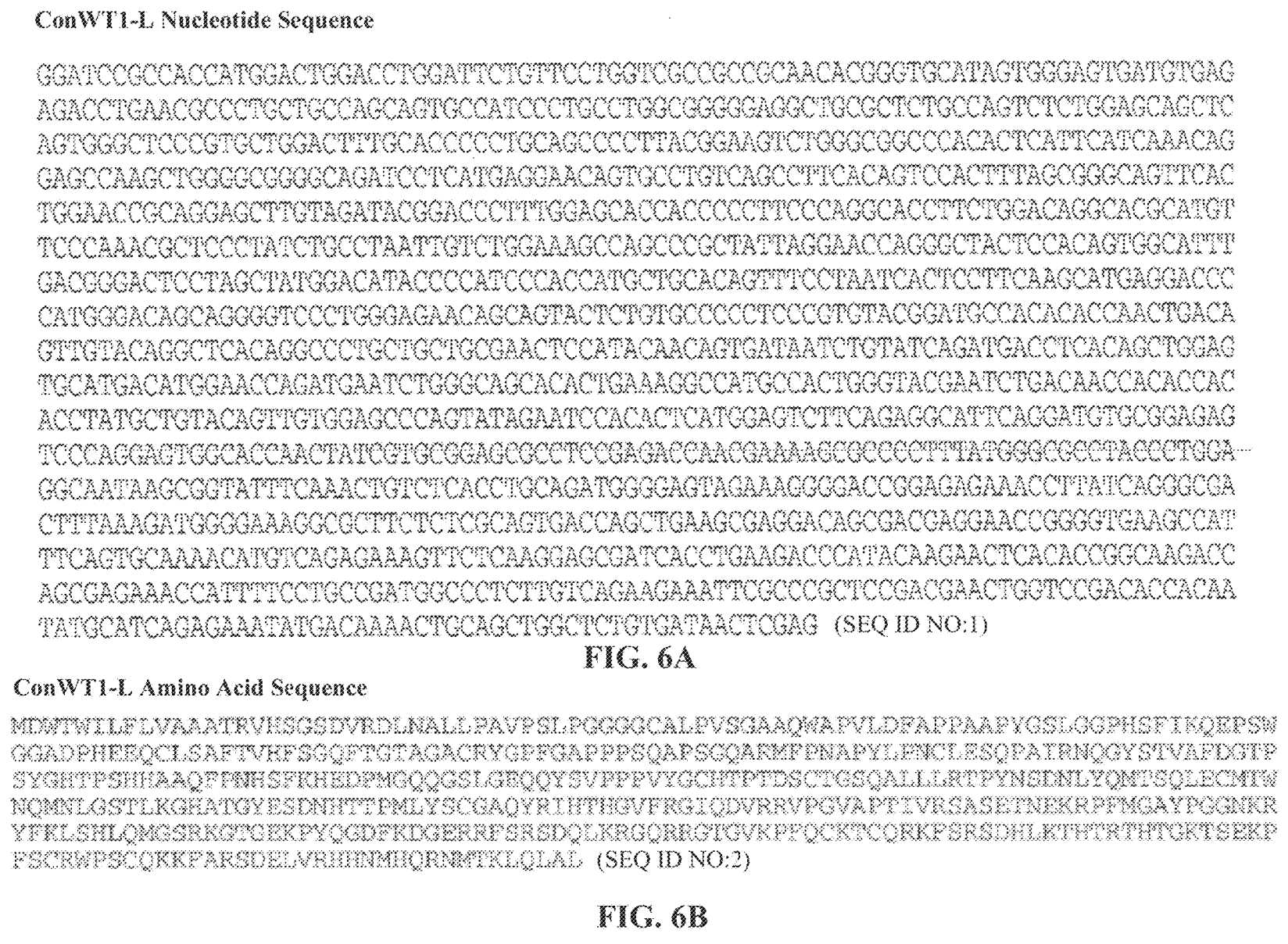

The WT1 consensus antigen can be the nucleic acid SEQ ID NO:1, which encodes SEQ ID NO:2 (FIGS. 6A and 6B). In some embodiments, the WT1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO:1. In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:2.

In still other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:2, provided that residues 312, 317, 342, and 347 of SEQ ID NO:2 are any residue other than cysteine (C) and residues 330, 334, 360, and 364 of SEQ ID NO:2 are any residue other than histidine (H). In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:2, provided that residues 312, 317, 330, 334, 342, 347, 360, and 364 of SEQ ID NO:2 are glycine (G).

The WT1 consensus antigen can be the amino acid sequence SEQ ID NO:2. In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:2. The WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:2, provided that residues 312, 317, 342, and 347 of SEQ ID NO:2 are any residue other than cysteine (C) and residues 330, 334, 360, and 364 of SEQ ID NO:2 are any residue other than histidine (H). In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:2, provided that residues 312, 317, 330, 334, 342, 347, 360, and 364 of SEQ ID NO:2 are glycine (G).

The WT1 consensus antigen can be the nucleic acid SEQ ID NO:3, which encodes SEQ ID NO:4 (FIGS. 7A and 7B). In some embodiments, the WT1 consensus antigen can be the nucleic acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the nucleic acid sequence set forth in SEQ ID NO:3. In other embodiments, the WT1 consensus antigen can be the nucleic acid sequence that encodes the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:4.

The WT1 consensus antigen can be the amino acid sequence SEQ ID NO:4. In some embodiments, the WT1 consensus antigen can be the amino acid sequence having at least about 80%, 81%, 82%, 83%, 84%, 85%, 86%, 87%, 88%, 89%, 90%, 91%, 92%, 93%, 94%, 95%, 96%, 97%, 98%, or 99% identity over an entire length of the amino acid sequence set forth in SEQ ID NO:4.

Immunogenic fragments of SEQ ID NO:2 and SEQ ID NO:4 can be provided. Immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2 and/or SEQ ID NO:4. In some embodiments, immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2, provided that if residues 312, 317, 342, and 347 of SEQ ID NO:2 are present in the immunogenic fragment, then these residues are any residue other than cysteine (C), and provided that if residues 330, 334, 360, and 364 of SEQ ID NO:2 are present in the immunogenic fragment, then these residues are any residue other than histidine (H). In other embodiments, immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:2, provided that if residues 312, 317, 330, 334, 342, 347, 360, and 364 of SEQ ID NO:2 are present in the immunogenic fragment, then these residues are glycine (G).

In some embodiments, immunogenic fragments include a leader sequence, for example, an immunoglobulin leader sequence, such as the immunoglobulin E (IgE) leader sequence. In some embodiments, immunogenic fragments are free of a leader sequence.

Immunogenic fragments of proteins with amino acid sequences having identity to immunogenic fragments of SEQ ID NO:2 and 4 can be provided. Such fragments can comprise at least 60%, at least 65%, at least 70%, at least 75%, at least 75%, at least 80%, at least 85%, at least 90%, at least 95%, at least 96%, at least 97%, at least 98%, or at least 99% of proteins having 95% or greater identity to SEQ ID NO:2 and/or SEQ ID NO:4. Some embodiments relate to immunogenic fragments that have 96% or greater identity to the immunogenic fragments of WT1 protein sequences herein. Some embodiments relate to immunogenic fragments that have 97% or greater identity to the immunogenic fragments of WT1 protein sequences herein. Some embodiments relate to immunogenic fragments that have 98% or greater identity to the immunogenic fragments of WT1 protein sequences herein. Some embodiments relate to immunogenic fragments that have 99% or greater identity to the immunogenic fragments of WT1 protein sequences herein. In some embodiments, immunogenic fragments include a leader sequence, for example, an immunoglobulin leader sequence such as the IgE leader sequence. In some embodiments, the immunogenic fragments are free of a leader sequence.

Some embodiments relate to immunogenic fragments of SEQ ID NO:1 and SEQ ID NO:3. Immunogenic fragments can comprise at least 60%, at least 65%, at least 70%, at least 75%, at least 80%, at least 85%, at least 90%, at least 95%, at least 96%, at least 97%, at least 98%, or at least 99% of SEQ ID NO:1 and/or SEQ ID NO:3. In some embodiments, immunogenic fragments include sequences that encode a leader sequence, for example, an immunoglobulin leader sequence such as the IgE leader sequence. In some embodiments, immunogenic fragments are free of coding sequences that encode a leader sequence. Immunogenic fragments of nucleic acids with nucleotide sequences having identity to immunogenic fragments of SEQ ID NO:1 and SEQ ID NO:3 can be provided. Such fragments can comprise at least 60%, at least 65%, at least 70%, at least 75%, at least 75%, at least 80%, at least 85%, at least 90%, at least 95%, at least 96%, at least 97%, at least 98%, or at least 99% of nucleic acids having 95% or greater identity to SEQ ID NO:1 and/or SEQ ID NO:3. Some embodiments relate to immunogenic fragments that have 96% or greater identity to the immunogenic fragments of WT1 nucleic acid sequences herein. Some embodiments relate to immunogenic fragments that have 97% or greater identity to the immunogenic fragments of WT1 nucleic acid sequences herein. Some embodiments relate to immunogenic fragments that have 98% or greater identity to the immunogenic fragments of WT1 nucleic acid sequences herein. Some embodiments relate to immunogenic fragments that have 99% or greater identity to the immunogenic fragments of WT1 nucleic sequences herein. In some embodiments, immunogenic fragments include sequences that encode a leader sequence, for example, an immunoglobulin leader sequence such as the IgE leader sequence. In some embodiments, immunogenic fragments are free of coding sequences that encode a leader sequence.

b. Vector

The vaccine can comprise one or more vectors that include a heterologous nucleic acid encoding the antigen. The one or more vectors can be capable of expressing the antigen in a quantity effective to elicit an immune response in the mammal. The vector may comprise heterologous nucleic acid encoding the antigen. The vector can have a nucleic acid sequence containing an origin of replication. The vector can be a plasmid, bacteriophage, bacterial artificial chromosome or yeast artificial chromosome. The vector can be either a self-replication extra chromosomal vector, or a vector which integrates into a host genome.

The one or more vectors can be an expression construct, which is generally a plasmid that is used to introduce a specific gene into a target cell. Once the expression vector is inside the cell, the protein that is encoded by the gene is produced by the cellular-transcription and translation machinery ribosomal complexes. The plasmid is frequently engineered to contain regulatory sequences that act as enhancer and promoter regions and lead to efficient transcription of the gene carried on the expression vector. The vectors of the present invention express large amounts of stable messenger RNA, and therefore proteins.

The vectors may have expression signals such as a strong promoter, a strong termination codon, adjustment of the distance between the promoter and the cloned gene, and the insertion of a transcription termination sequence and a PTIS (portable translation initiation sequence).

(1) Expression Vectors

The vector can be a circular plasmid or a linear nucleic acid. The circular plasmid and linear nucleic acid are capable of directing expression of a particular nucleotide sequence in an appropriate subject cell. The vector can have a promoter operably linked to the antigen-encoding nucleotide sequence, which may be operably linked to termination signals. The vector can also contain sequences required for proper translation of the nucleotide sequence. The vector comprising the nucleotide sequence of interest may be chimeric, meaning that at least one of its components is heterologous with respect to at least one of its other components. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development.

(2) Plasmid

The vector can be a plasmid. The plasmid may be useful for transfecting cells with nucleic acid encoding the antigen, which the transformed host cells is cultured and maintained under conditions wherein expression of the antigen takes place.

The plasmid may comprise a nucleic acid sequence that encodes one or more of the various antigens disclosed above including coding sequences that encode synthetic, consensus antigen capable of eliciting an immune response against an antigen, fragments of such proteins, variants of such proteins, fragments of variants or fusion proteins which are made up of combinations of consensus proteins and/or fragments of consensus protein and/or variants of consensus protein and/or fragments of variants consensus proteins.

A single plasmid may contain coding sequence for a single antigen, coding sequence for two antigens, coding sequence for three antigens or coding sequence for four antigens.

In some embodiments, a plasmid may further comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence. The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and W094/016737, the contents of each are fully incorporated by reference.

The plasmid may also comprise a mammalian origin of replication in order to maintain the plasmid extrachromosomally and produce multiple copies of the plasmid in a cell. The plasmid may be p V AXI, pCEP4 or pREP4 from Invitrogen (San Diego, CA), which may comprise the Epstein Barr virus origin of replication and nuclear antigen EBNA-1 coding region, which may produce high copy episomal replication without integration. The backbone of the plasmid may be pA V0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5" of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

(3) Circular and Linear Vectors

The vector may be circular plasmid, which may transform a target cell by integration into the cellular genome or exist extrachromosomally (e.g., autonomous replicating plasmid with an origin of replication).

The vector can be pVAX, pcDNA3.0, or provax, or any other expression vector capable of expressing DNA encoding the antigen and enabling a cell to translate the sequence to an antigen that is recognized by the immune system.

Also provided herein is a linear nucleic acid vaccine, or linear expression cassette ("LEC"), that is capable of being efficiently delivered to a subject via electroporation and expressing one or more desired antigens. The LEC may be any linear DNA devoid of any phosphate backbone. The DNA may encode one or more antigens. The LEC may contain a promoter, an intron, a stop codon, and/or a polyadenylation signal. The expression of the antigen may be controlled by the promoter. The LEC may not contain any antibiotic resistance genes and/or a phosphate backbone. The LEC may not contain other nucleic acid sequences unrelated to the desired antigen gene expression.

The LEC may be derived from any plasmid capable of being linearized. The plasmid may be capable of expressing the antigen. The plasmid can be pNP (Puerto Rico/34) or pM2 (New Caledonia/99). The plasmid may be WLV009, pVAX, pcDNA3.0, or provax, or any other expression vector capable of expressing DNA encoding the antigen and enabling a cell to translate the sequence to an antigen that is recognized by the immune system.

The LEC can be pcrM2. The LEC can be pcrNP. pcrNP and pcrMR can be derived from pNP (Puerto Rico/34) and pM2 (New Caledonia/99), respectively.

(4) Promoter, Intron, Stop Codon, and Polyadenylation Signal

The vector may have a promoter. A promoter may be any promoter that is capable of driving gene expression and regulating expression of the isolated nucleic acid. Such a promoter is a cis-acting sequence element required for transcription via a DNA dependent RNA polymerase, which transcribes the antigen sequence described herein. Selection of the promoter used to direct expression of a heterologous nucleic acid depends on the particular application. The promoter may be positioned about the same distance from the transcription start in the vector as it is from the transcription start site in its natural setting. However, variation in this distance may be accommodated without loss of promoter function.

The promoter may be operably linked to the nucleic acid sequence encoding the antigen and signals required for efficient polyadenylation of the transcript, ribosome binding sites, and translation termination.

The promoter may be a CMV promoter, SV40 early promoter, SV40 later promoter, metallothionein promoter, murine mammary tumor virus promoter, Rous sarcoma virus promoter, polyhedrin promoter, or another promoter shown effective for expression in eukaryotic cells.

The vector may include an enhancer and an intron with functional splice donor and acceptor sites. The vector may contain a transcription termination region downstream of the structural gene to provide for efficient termination. The termination region may be obtained from the same gene as the promoter sequence or may be obtained from different genes.

(5) Method of Preparing the Vector

Provided herein is a method for preparing the vector that comprise the DNA vaccines discussed herein. The vector, after the final subcloning step into the mammalian expression plasmid, can be used to inoculate a cell culture in a large scale fermentation tank, using known methods in the art.

The vector for use with the EP devices, which are described below in more detail, can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

c. Excipients and Other Components of the Vaccine

The vaccine may further comprise a pharmaceutically acceptable excipient. The pharmaceutically acceptable excipient can be functional molecules such as vehicles, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. The DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be one or more adjuvants. The adjuvant can be other genes that are expressed in an alternative plasmid or are delivered as proteins in combination with the plasmid above in the vaccine. The one or more adjuvants may be selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, IL-28, MHC, CD80, CD86, IL-1, IL-2, IL-4, IL-5, IL-6, IL-10, IL-18, MCP-1, MIP-1a, MIP-1~, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2, IL-15 having the signal sequence or coding sequence that encodes the signal sequence deleted and optionally including a different signal peptide such as that from IgE or coding sequence that encodes a different signal peptide such as that from IgE, and functional fragments thereof, or a combination thereof. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

In some embodiments adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/USIO/ 048827, which are each incorporated herein by reference. Examples of iL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. and Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/ 024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

Other genes that can be useful as adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine may further comprise a genetic vaccine facilitator agent as described in U.S. Ser. No. 021,579 filed Apr. 1, 1994, which is fully incorporated by reference.

The vaccine may comprise the antigen and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, vaccine according to the present invention comprise about 5 nanogram to about 1000 micrograms of DNA. In some preferred embodiments, vaccine can contain about 10 nanograms to about 800 micrograms of DNA. In some preferred embodiments, the vaccine can contain about 0.1 to about 500 micrograms of DNA. In some preferred embodiments, the vaccine can contain about 1 to about 350 micrograms of DNA. In some preferred embodiments, the vaccine can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the antigen or plasmid thereof.

The vaccine can be formulated according to the mode of administration to be used. An injectable vaccine pharmaceutical composition can be sterile, pyrogen free and particulate free. An isotonic formulation or solution can be used. Additives for isotonicity can include sodium chloride, dextrose, mannitol, sorbitol, and lactose. The vaccine can comprise a vasoconstriction agent. The isotonic solutions can include phosphate buffered saline. Vaccine can further comprise stabilizers including gelatin and albumin. The stabilizers can allow the formulation to be stable at room or ambient temperature for extended periods of time, including LGS or polycations or polyanions.

3. Method of Delivery of the Vaccine

Provided herein is a method for delivering the vaccine for providing genetic constructs and antigens, which comprise epitopes that make them particular effective against target immunogens against which an immune response can be induced. The method of delivering the vaccine or vaccination may be provided to induce a therapeutic and prophylactic immune response. The vaccination process may generate in the mammal an immune response against the antigen. The vaccine may be delivered to an individual to modulate the activity of the mammal's immune system and enhance the immune response. The delivery of the vaccine may be the transfection of the antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against the antigen by administering to the mammals the vaccine as discussed above.

Upon delivery of the vaccine and plasmid into the cells of the mammal, the transfected cells will express and secrete the antigen for each of the plasmids injected from the vaccine. This antigen will be recognized as foreign by the immune system and antibodies will be made against them. These antibodies will be maintained by the immune system and allow for an effective response against the antigen.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatment

The vaccine may be administered in combination with other proteins and/or genes encoding CCL20, a-interferon, y-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-10, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DRS, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAPI, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL20, IL-12 protein, IL-15 protein, IL-28 protein, CTACKprotein, TECK protein, MEC protein or RANTES protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the vaccine may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The antigen or immunogen may be delivered via DNA injection and along with in vivo electroporation.

b. Electroporation

The vaccine can be formulated in accordance with standard techniques well known to those skilled in the pharmaceutical art. Such compositions can be administered in dosages and by techniques well known to those skilled in the medical arts taking into consideration such factors as the age, sex, weight, and condition of the particular subject, and the route of administration. The subject can be a mammal, such as a human, a horse, a cow, a pig, a sheep, a cat, a dog, a rat, or a mouse.

The vaccine can be administered prophylactically or therapeutically. In prophylactic administration, the vaccines can be administered in an amount sufficient to induce an immune response. In therapeutic applications, the vaccines are administered to a subject in need thereof in an amount sufficient to elicit a therapeutic effect. An amount adequate to accomplish this is defined as "therapeutically effective dose." Amounts effective for this use will depend on, e.g., the particular composition of the vaccine regimen administered, the manner of administration, the stage and severity of the disease, the general state of health of the patient, and the judgment of the prescribing physician.

The vaccine can be administered by methods well known in the art as described in Donnelly et al. (Ann. Rev. Immunol. 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), the contents of all of which are incorporated herein by reference in their entirety. The DNA of the vaccine can be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The vaccine can be delivered via a variety of routes. Typical delivery routes include parenteral administration, e.g., intradermal, intramuscular or subcutaneous delivery. Other routes include oral administration, intranasal, and intravaginal routes. For the DNA of the vaccine in particular, the vaccine can be delivered to the interstitial spaces of tissues of an individual (Felgner et al., U.S. Pat. Nos. 5,580,859 and 5,703,055, the contents of all of which are incorporated herein by reference in their entirety). The vaccine can also be administered to muscle, or can be administered via intradermal or subcutaneous injections, or transdermally, such as by iontophoresis. Epidermal administration of the vaccine can also be employed. Epidermal administration can involve mechanically or chemically irritating the outermost layer of epidermis to stimulate an immune response to the irritant (Carson et al., U.S. Pat. No. 5,679,647, the contents of which are incorporated herein by reference in its entirety).

The vaccine can also be formulated for administration via the nasal passages. Formulations suitable for nasal administration, wherein the carrier is a solid, can include a coarse powder having a particle size, for example, in the range of about 10 to about 500 microns which is administered in the manner in which snuff is taken, i.e., by rapid inhalation through the nasal passage from a container of the powder held close up to the nose. The formulation can be a nasal spray, nasal drops, or by aerosol administration by nebulizer. The formulation can include aqueous or oily solutions of the vaccine.

The vaccine can be a liquid preparation such as a suspension, syrup or elixir. The vaccine can also be a preparation for parenteral, subcutaneous, intradermal, intramuscular or intravenous administration (e.g., injectable administration), such as a sterile suspension or emulsion.

The vaccine can be incorporated into liposomes, microspheres or other polymer matrices (Felgner et al., U.S. Pat. No. 5,703,055; Gregoriadis, Liposome Technology, Vols. I to III (2nd ed. 1993), the contents of which are incorporated herein by reference in their entirety). Liposomes can consist of phospholipids or other lipids, and can be nontoxic, physiologically acceptable and metabolizable carriers that are relatively simple to make and administer.

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, PA) or Elgen electroporator (Genetronics, San Diego, CA) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is predelineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

The vaccine can be administered via electroporation, such as by a method described in U.S. Pat. No. 7,664,545, the contents of which are incorporated herein by reference. The electroporation can be by a method and/or apparatus described in U.S. Pat. Nos. 6,302,874; 5,676,646; 6,241, 701; 6,233,482; 6,216,034; 6,208,893; 6,192,270; 6,181, 964; 6,150,148; 6,120,493; 6,096,020; 6,068,650; and 5,702,359, the contents of which are incorporated herein by reference in their entirety. The electroporation may be carried out via a minimally invasive device.

The minimally invasive electroporation device ("MID") may be an apparatus for injecting the vaccine described above and associated fluid into body tissue. The device may comprise a hollow needle, DNA cassette, and fluid delivery means, wherein the device is adapted to actuate the fluid delivery means in use so as to concurrently (for example, automatically) inject DNA into body tissue during insertion of the needle into the said body tissue. This has the advantage that the ability to inject the DNA and associated fluid gradually while the needle is being inserted leads to a more even distribution of the fluid through the body tissue. The pain experienced during injection may be reduced due to the distribution of the DNA being injected over a larger area.

The MID may inject the vaccine into tissue without the use of a needle. The MID may inject the vaccine as a small stream or jet with such force that the vaccine pierces the surface of the tissue and enters the underlying tissue and/or muscle. The force behind the small stream or jet may be provided by expansion of a compressed gas, such as carbon dioxide through a micro-orifice within a fraction of a second. Examples of minimally invasive electroporation devices, and methods of using them, are described in published U.S. Patent Application No. 20080234655; U.S. Pat. Nos. 6,520, 950; 7,171,264; 6,208,893; 6,009,347; 6,120,493; 7,245, 963; 7,328,064; and 6,763,264, the contents of each of which are herein incorporated by reference.

The MID may comprise an injector that creates a high-speed jet of liquid that painlessly pierces the tissue. Such needle-free injectors are commercially available. Examples of needle-free injectors that can be utilized herein include those described in U.S. Pat. Nos. 3,805,783; 4,447,223; 5,505,697; and 4,342,310, the contents of each of which are herein incorporated by reference.

A desired vaccine in a form suitable for direct or indirect electrotransport may be introduced (e.g., injected) using a needle-free injector into the tissue to be treated, usually by contacting the tissue surface with the injector so as to actuate delivery of a jet of the agent, with sufficient force to cause penetration of the vaccine into the tissue. For example, if the tissue to be treated is mucosa, skin or muscle, the agent is projected towards the mucosal or skin surface with sufficient force to cause the agent to penetrate through the stratum corneum and into dermal layers, or into underlying tissue and muscle, respectively.

Needle-free injectors are well suited to deliver vaccines to all types of tissues, particularly to skin and mucosa. In some embodiments, a needle-free injector may be used to propel a liquid that contains the vaccine to the surface and into the subject's skin or mucosa. Representative examples of the various types of tissues that can be treated using the invention methods include pancreas, larynx, nasopharynx, hypopharynx, oropharynx, lip, throat, lung, heart, kidney, muscle, breast, colon, prostate, thymus, testis, skin, mucosal tissue, ovary, blood vessels, or any combination thereof.

The MID may have needle electrodes that electroporate the tissue. By pulsing between multiple pairs of electrodes in a multiple electrode array, for example set up in rectangular or square patterns, provides improved results over that of pulsing between a pair of electrodes. Disclosed, for example, in U.S. Pat. No. 5,702,359 entitled "Needle Electrodes for Mediated Delivery of Drugs and Genes" is an array of needles wherein a plurality of pairs of needles may be pulsed during the therapeutic treatment. In that application, which is incorporated herein by reference as though fully set forth, needles were disposed in a circular array, but have connectors and switching apparatus enabling a pulsing between opposing pairs of needle electrodes. A pair of needle electrodes for delivering recombinant expression vectors to cells may be used. Such a device and system is described in U.S. Pat. No. 6,763,264, the contents of which are herein incorporated by reference. Alternatively, a single needle device may be used that allows injection of the DNA and electroporation with a single needle resembling a normal injection needle and applies pulses of lower voltage than those delivered by presently used devices, thus reducing the electrical sensation experienced by the patient.

The MID may comprise one or more electrode arrays. The arrays may comprise two or more needles of the same diameter or different diameters. The needles may be evenly or unevenly spaced apart. The needles may be between 0.005 inches and 0.03 inches, between 0.01 inches and 0.025 inches; or between 0.015 inches and 0.020 inches. The needle may be 0.0175 inches in diameter. The needles may be 0.5 mm, 1.0 mm, 1.5 mm, 2.0 mm, 2.5 mm, 3.0 mm, 3.5 mm, 4.0 mm, or more spaced apart.

The MID may consist of a pulse generator and a two or more-needle vaccine injectors that deliver the vaccine and electroporation pulses in a single step. The pulse generator may allow for flexible programming of pulse and injection parameters via a flash card operated personal computer, as well as comprehensive recording and storage of electroporation and patient data. The pulse generator may deliver a variety of volt pulses during short periods of time. For example, the pulse generator may deliver three 15 volt pulses of 100 ms in duration. An example of such a MID is the Elgen 1000 system by Inovio Biomedical Corporation, which is described in U.S. Pat. No. 7,328,064, the contents of which are herein incorporated by reference.

The MID may be a CELLECTRA (Inovio Pharmaceuticals, Blue Bell PA) device and system, which is a modular electrode system, that facilitates the introduction of a macromolecule, such as a DNA, into cells of a selected tissue in a body or plant. The modular electrode system may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The macromolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the macromolecule into the cell between the plurality of electrodes. Cell death due to overheating of cells is minimized by limiting the power dissipation in the tissue by virtue of constant-current pulses. The Cellectra device and system is described in U.S. Pat. No. 7,245,963, the contents of which are herein incorporated by reference.

The MID may be an Elgen 1000 system (Inovio Pharmaceuticals). The Elgen 1000 system may comprise device that provides a hollow needle; and fluid delivery means, wherein the apparatus is adapted to actuate the fluid delivery means in use so as to concurrently (for example automatically) inject fluid, the described vaccine herein, into body tissue during insertion of the needle into the said body tissue. The advantage is the ability to inject the fluid gradually while the needle is being inserted leads to a more even distribution of the fluid through the body tissue. It is also believed that the pain experienced during injection is reduced due to the distribution of the volume of fluid being injected over a larger area.

In addition, the automatic injection of fluid facilitates automatic monitoring and registration of an actual dose of fluid injected. This data can be stored by a control unit for documentation purposes if desired.

It will be appreciated that the rate of injection could be either linear or non-linear and that the injection may be carried out after the needles have been inserted through the skin of the subject to be treated and while they are inserted further into the body tissue.

Suitable tissues into which fluid may be injected by the apparatus of the present invention include tumor tissue, skin or liver tissue but may be muscle tissue.

The apparatus further comprises needle insertion means for guiding insertion of the needle into the body tissue. The rate of fluid injection is controlled by the rate of needle insertion. This has the advantage that both the needle insertion and injection of fluid can be controlled such that the rate of insertion can be matched to the rate of injection as desired. It also makes the apparatus easier for a user to operate. If desired means for automatically inserting the needle into body tissue could be provided.

A user could choose when to commence injection of fluid. Ideally however, injection is commenced when the tip of the needle has reached muscle tissue and the apparatus may include means for sensing when the needle has been inserted to a sufficient depth for injection of the fluid to commence. This means that injection of fluid can be prompted to commence automatically when the needle has reached a desired depth (which will normally be the depth at which muscle tissue begins). The depth at which muscle tissue begins could for example be taken to be a preset needle insertion depth such as a value of 4 mm which would be deemed sufficient for the needle to get through the skin layer.

The sensing means may comprise an ultrasound probe. The sensing means may comprise a means for sensing a change in impedance or resistance. In this case, the means may not as such record the depth of the needle in the body tissue but will rather be adapted to sense a change in impedance or resistance as the needle moves from a different type of body tissue into muscle. Either of these alternatives provides a relatively accurate and simple to operate means of sensing that injection may commence. The depth of insertion of the needle can further be recorded if desired and could be used to control injection of fluid such that the volume of fluid to be injected is determined as the depth of needle insertion is being recorded.

The apparatus may further comprise: a base for supporting the needle; and a housing for receiving the base therein, wherein the base is moveable relative to the housing such that the needle is retracted within the housing when the base is in a first rearward position relative to the housing and the needle extends out of the housing when the base is in a second forward position within the housing. This is advantageous for a user as the housing can be lined up on the skin of a patient, and the needles can then be inserted into the patient's skin by moving the housing relative to the base.

As stated above, it is desirable to achieve a controlled rate of fluid injection such that the fluid is evenly distributed over the length of the needle as it is inserted into the skin. The fluid delivery means may comprise piston driving means adapted to inject fluid at a controlled rate. The piston driving means could for example be activated by a servo motor. However, the piston driving means may be actuated by the base being moved in the axial direction relative to the housing. It will be appreciated that alternative means for fluid delivery could be provided. Thus, for example, a closed container which can be squeezed for fluid delivery at a controlled or non-controlled rate could be provided in the place of a syringe and piston system.

The apparatus described above could be used for any type of injection. It is however envisaged to be particularly useful in the field of electroporation and so it may further comprises means for applying a voltage to the needle. This allows the needle to be used not only for injection but also as an electrode during, electroporation. This is particularly advantageous as it means that the electric field is applied to the same area as the injected fluid. There has traditionally been a problem with electroporation in that it is very difficult to accurately align an electrode with previously injected fluid and so users have tended to inject a larger volume of fluid than is required over a larger area and to apply an electric field over a higher area to attempt to guarantee an overlap between the injected substance and the electric field. Using the present invention, both the volume of fluid injected and the size of electric field applied may be reduced while achieving a good fit between the electric field and the fluid.

4. Method of Treatment and/or Prevention

Also provided herein is a method of treating, protecting against, and/or preventing disease in a subject in need thereof by administering the vaccine to a subject in need thereof. The disease can be cancer, for example, Wilm's tumor, metastatic cancer arising from Wilm's tumor, and a WT1-expressing cancer or tumor. The vaccine can be administered to the subject as described above in the method of delivery. Administration of the vaccine to the subject can induce or elicit an immune response in the subject. In particular, administration of the vaccine to the subject can induce or elicit a humoral and/or cellular immune response in the subject.

In particular, the method can treat a subject having a Wilm's tumor, metastatic cancer arising from a Wilm's tumor, and/or a WT1-expressing tumor or cancer because the vaccine slows the growth, reduces, and eliminates the Wilm's tumor, metastatic cancer arising from a Wilm's tumor, and/or the WT1-expressing tumor or cancer. The method can also prevent Wilm's tumor, metastatic cancer arising from the Wilm's tumor, and/or a WT1-expressing tumor or cancer in the subject because the vaccine inhibits formation and growth of the Wilm's tumor, metastatic cancer arising from the Wilm's tumor, and/or WT1-expressing tumor or cancer. As described above, the vaccine induces or elicits a humoral and/or cellular immune response. This induced humoral and/or cellular immune response can target the Wilm's tumor, metastatic cancer arising from the Wilm's tumor, and/or WT1-expressing tumor or cancer, thereby slowing the growth of, reducing, and eliminating any Wilm's tumor, metastatic cancer arising from the Wilm's tumor, and/or WT1-expressing tumors or cancers in the subject administered the vaccine. This humoral and/or cellular immune response induced by the vaccine can also inhibit the formation and growth of any Wilm's tumor, metastatic cancer arising from the Wilm's tumor, and/or WT-1 expressing tumors or cancers in the subject administered the vaccine.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

The present invention has multiple aspects, illustrated by the following non-limiting examples.

5. Examples

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

A stepwise approach was taken as described here in the Examples to generate an WT1 immunogen. The WT1 gene was modified through several stepwise modifications. First, the WT1 RNA structure was modified so that it produced a single, full-length transcript. Second, codon usage was modified in order to alter the RNA structure at the 5' end and thereby improve in vivo expression. Finally, the zinc finger domain of the gene was mutated so as to modify WT1 activity and to delete portions of the zinc finger binding site.

Example 1

Optimized WT-1

A stepwise approach to generate a WT1 immunogen was developed. First changes to the RNA structure was designed that resulted in only a single full length transcript being produced, thus creating an immunogen with a much more controlled phenotype. Sequences also contained modified codon use selection and altered RNA structure at the 5' end to improve expression in vivo. Accordingly, the WT1 immunogen was optimized for expression. A plasmid was generated that encoded an expression cassette for this improved immunogen and was tested in animals for immunization potential and the ability to generate T cell and B cell responses. This plasmid vaccine was formulated for enhanced delivery in vivo by electroporation and specific conditions were used for in vivo delivery.

Plasmids encoding this immunogen (referred to as WT1-pVAX1, WT1-pVAX2, WT1-pVAX3, WT1-pVAX4 and WT1-pVAX5) was compared to a WT1 vaccine that represented the standard vaccine being studied by the field (referred to as WT1-pCDNA1, WT1-pCDNA2, WT1-pCDNA3, WT1-pCDNA4 and WT1-pCDNA5).

Mouse studies were conducted. Mice were vaccinated with the modified WT1 vaccine (i.e., the vectors WT1-pVAX1, WT1-pVAX2, WT1-pVAX3, WT1-pVAX4 and WT1-pVAX5) and experienced greater anti-WT1 T and B cell responses than did mice vaccinated with standard WT1 vaccines that comprise native WT1 (i.e., WT1-pCDNA1, WT1-pCDNA2, WT1-pCDNA3, WT1-pCDNA4 and WT1-pCDNA5).

Figure 2:
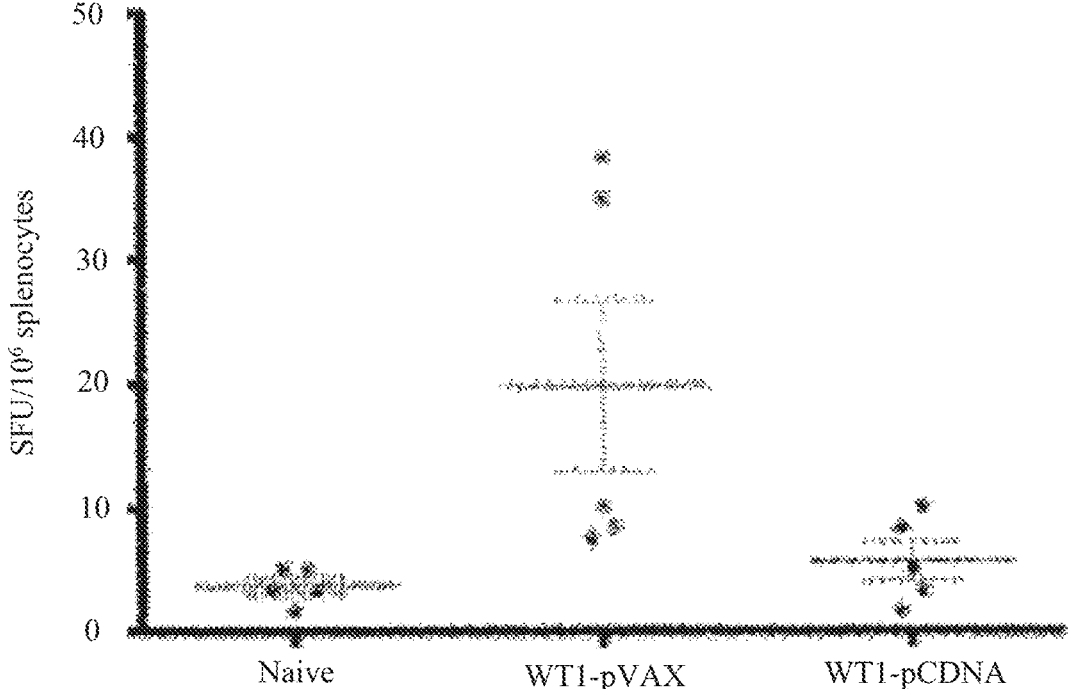
FIG. 2 shows a graph plotting immunization group vs. SFU per $10^6$ splenocytes.

Animals (i.e., BalB/C mice) were immunized 3× with identical amounts of WT-1 plasmid, either the new WT1-pVax vaccine (i.e., the vectors WT1-pVAX1, WT1-pVAX2, WT1-pVAX3, WT1-pVAX4 and WT1-pVAX5) or the original WT-1 plasmid vaccine (i.e., WT1-pCDNA1, WT1-pCDNA2, WT1-pCDNA3, WT1-pCDNA4 and WT1-pCDNA5). The results for T cell assays (i.e., interferon-gamma (IFN-γ ELISpot assay) are shown in FIGS. 1 and 2. It was clear that the new designed WT-1 vaccine (i.e., the vectors WT1-pVAX1, WT1-pVAX2, WT1-pVAX3, WT1-pVAX4 and WT1-pVAX5) was approximately 4-fold superior in generating T cell responses than the WT-1 original vaccine (i.e., WT1-pCDNA1, WT1-pCDNA2, WT1-pCDNA3, WT1-pCDNA4 and WT1-pCDNA5). As shown in FIGS. 1 and 2, only low level or non-functional T cell immunity was observed with the standard vaccine, which was consistent with data that has been previously achieved.

Figure 3:
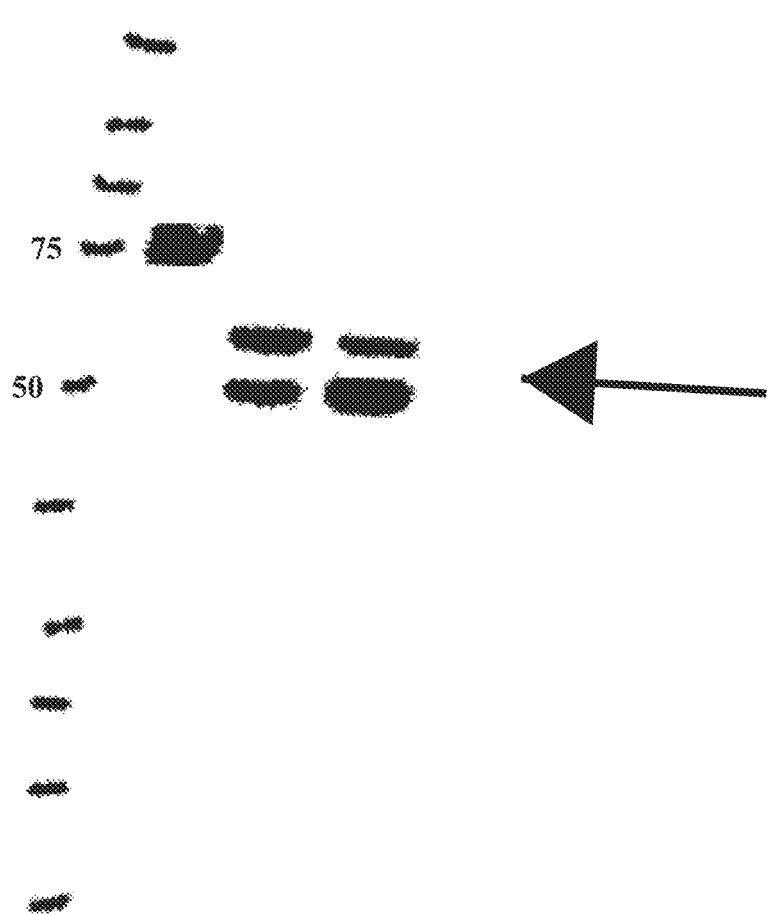
FIG. 3 shows an immunoblot.

The ability of this new DNA vaccine to induce antibody responses was also examined. These studies were performed by collecting sera from animals immunized in either the WT1-pCDNA or the WT1-pVAX vaccine. Seroconversion or the induction of antibody responses using the WT1-pCDNA vaccine was not observed (data not shown). In contrast the WT1-pVAX immunogen induced strong Western Blot reactivity with the correct specificity and molecular weight, showing robust WT1 seroconversion and strong antibody responses (FIG. 3). These data collectively strongly supported the improvement in this vaccine immunogene through delivery changes and improved design of the WT1 immunogen.

These data also showed that the conformational nature of the immunogen was maintained as these vaccines containing the optimized WT1 immunogen clearly reacted with native gene sequences in tumor cells.

The immunogen sequence was further targeted by modifying the coding sequence to destroy its native structure through two means, (1) targeting the Zinc Finger region and inducing mutations that modified WT1 activity as well as (2) deleting sequences from the important Zn finger binding site. These changes are outlined below in Examples 2 and 3.

Example 2

Consensus WT1

As described above, the optimized WT1 immunogen (i.e., the WT1 gene was optimized as described in Example 1) induced humoral and cellular immune responses. To further target or modify the WT1 immunogen sequence, a consensus WT1 immunogen was generated.

Figures 4, 5:
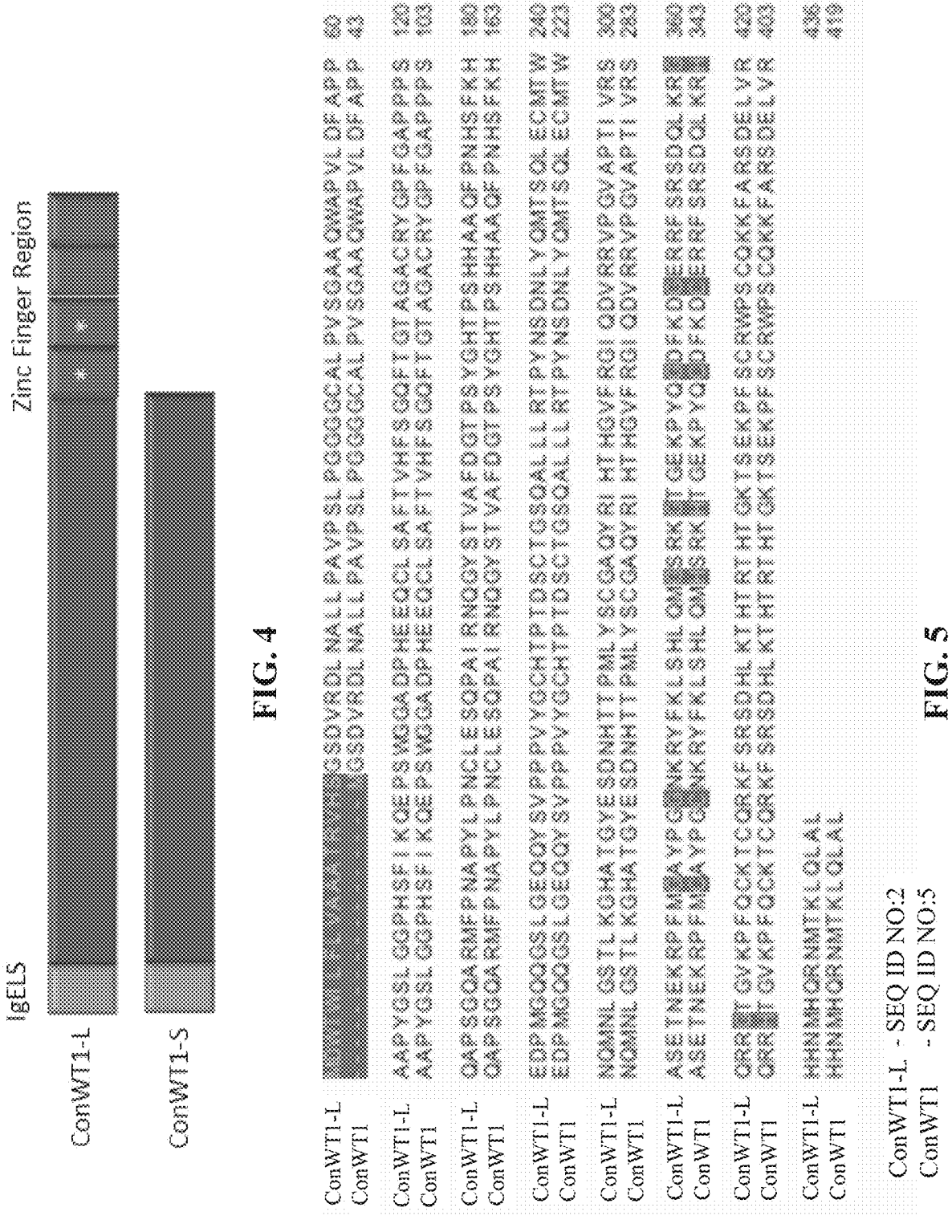
FIG. 4 shows a schematic of ConWT1-L and ConWT1-S.
FIG. 5 shows an alignment of the respective amino acid sequences of ConWT1-L and ConWT1.

Specifically, WT1 sequences from multiple species were compared to one another. As shown in Table 1 below, WT1 is highly conserved. Accordingly, WT1 sequences from multiple species were employed to generate a WT1 consensus sequence, in which the WT1 consensus sequence shared about 95% identity with human WT1. The resulting consensus WT1 immunogen (also referred to as ConWT1) shared 95.9% identity with human WT1 and has the amino acid sequence set forth in SEQ ID NO:5 (FIG. 5).

TABLE 1

| Identity of WT1 between Species. | | | | | |
|---|---|---|---|---|---|
| | Rhesus WT1 | Mouse WT1 | Rat WT1 | Pig WT1 | Chicken WT1 | Finch WT1 |
| Human WT1 | 99.50% | 97.50% | 97.80% | 97.80% | 91.30% | 91.30% |

Example 3

Zinc Finger Modification and Removal

The consensus WT1 immunogen described above in Example 2 was further modified to improve the immunogenicity of the WT1 immunogen. In particular, the consensus WT1 immunogen was modified to disrupt the zinc fingers located at the carboxy-terminus (C-terminus) of the WT1 immunogen. These modifications included substitution of the residues coordinating the zinc ion (i.e., CCHH motif) in the two amino-terminal (N-terminal) zinc fingers to yield a consensus WT1 immunogen with modified zinc fingers (also referred to herein as CON WT1 with modified zinc fingers or ConWT1-L) (FIGS. 4 and 5). The C and H residues of the CCHH motif were replaced with glycine (G). An immunoglobulin E (IgE) leader sequence was placed on the N-terminus of the ConWT1-L peptide. ConWT1-L is encoded by SEQ ID NO:1 and has the amino acid sequence set forth in SEQ ID NO:2 (FIGS. 6A and 6B, respectively).

FIG. 5 shows an alignment of the amino acid sequences of the consensus WT1 immunogen (ConWT1) and the consensus WT1 immunogen with modified zinc fingers (ConWT1-L). Shading in FIG. 5 indicates residues that differ between ConWT1 and ConWT1-L. Besides the addition of the IgE leader sequence to ConWT1-L, residues 312, 317, 330, 334, 342, 347, 360, and 364 in ConWT1-L differed from the corresponding residues in ConWT1 (i.e., residues 295, 300, 313, 317, 325, 330, 343, and 347). These differences reflected the modifications of the CCHH motifs in the two N-terminal zinc fingers described above.

Additionally, the consensus WT1 immunogen was modified to remove the zinc fingers to yield a consensus WT1 immunogen with no zinc fingers (also referred to herein as CON WT1 without zinc fingers or CONWT1-S) (FIG. 4). ConWT1-S is encoded by SEQ ID NO:3 and has the amino acid sequence set forth in SEQ ID NO:4 (FIGS. 7A and 7B, respectively).

Example 4

Expression Analysis of Constructs Encoding ConWT1-L and ConWT1-S

The nucleic acid sequence encoding ConWT1-L and ConWT1-S were separately placed in the pVAX1 vector (Life Technologies, Carlsbad, CA). The resulting vectors were named WT1-pVAX-L and WT1-pVAX-S, respectively. The WT1-pVAX-L and WT1-pVAX-S, along with pVAX1 were transfected into cells to confirm expression of ConWT1-L and ConWT1-S, respectively, from these vectors. pVAX1 served as a negative control.

Figure 8:
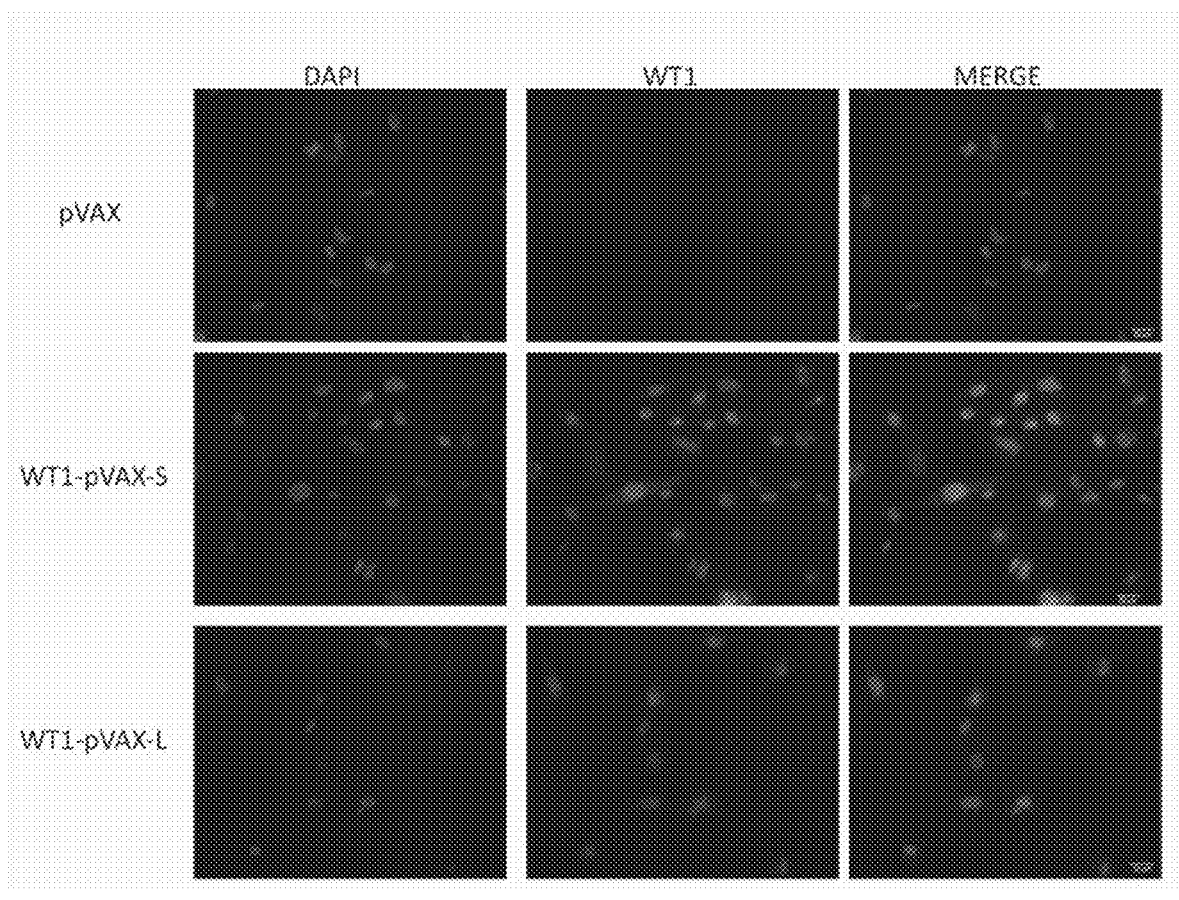
FIG. 8 shows staining of transfected cells.

After transfection, cells were stained with 4',6-Diamidino-2-Phenylindole (DAPI) to mark nuclei and antibody specific for WT1. FIG. 8 shows the results of this staining. In FIG. 8, the left and middle columns show the DAPI and WT1 staining, while the right column shows a merge of the DAPI and WT1 staining. No staining was detected with the WT1 antibody in cells transfected with pVAX1. These data indicated that both ConWT1-L and ConWT1-S were expressed from their respective vectors.

Figure 9:
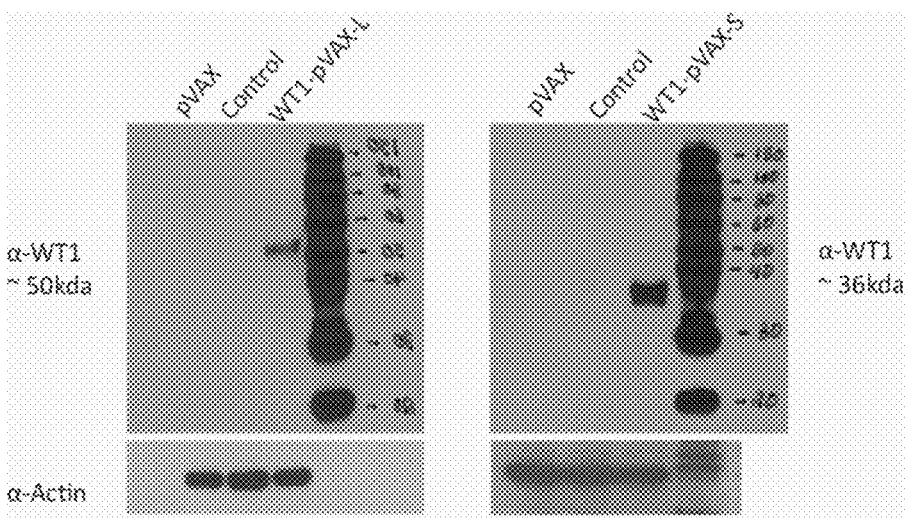
FIG. 9 shows immunoblots.

Expression of ConWT1-L and ConWT1-S was further confirmed by immunoblot of lysates derived from the transfected cells. Specifically, the immunoblots were probed with anti-WT1 antibody. As shown in FIG. 9, the expected sizes were detected for ConWT1-L and ConWT1-S (see lanes labeled WT1-pVAX-L and WT1-pVAX-S, respectively). No signal was detected in lysates obtained from cells transfected with pVAX1. Accordingly, these data further indicated that ConWT1-L and ConWT1-S were expressed within the transfected cells.

Example 5

Immune Response Induced by Constructs Encoding ConWT1-L and ConWT1-S

To determine if the constructs encoding ConWT1-L and ConWT1-S induced an immune response, C57BL/6 mice immunized with 25 μg WT1-pVAX-L or WT1-pVAX-S, respectively. C57BL/6 mice were also immunized 25 μg WT1-pVAX, which was the optimized construct encoding WT1 described in Example 1, or 25 μg WT1-pCDNA, which was a non-optimized construct encoding WT1. Naïve mice served as control.

Figures 10, 11:
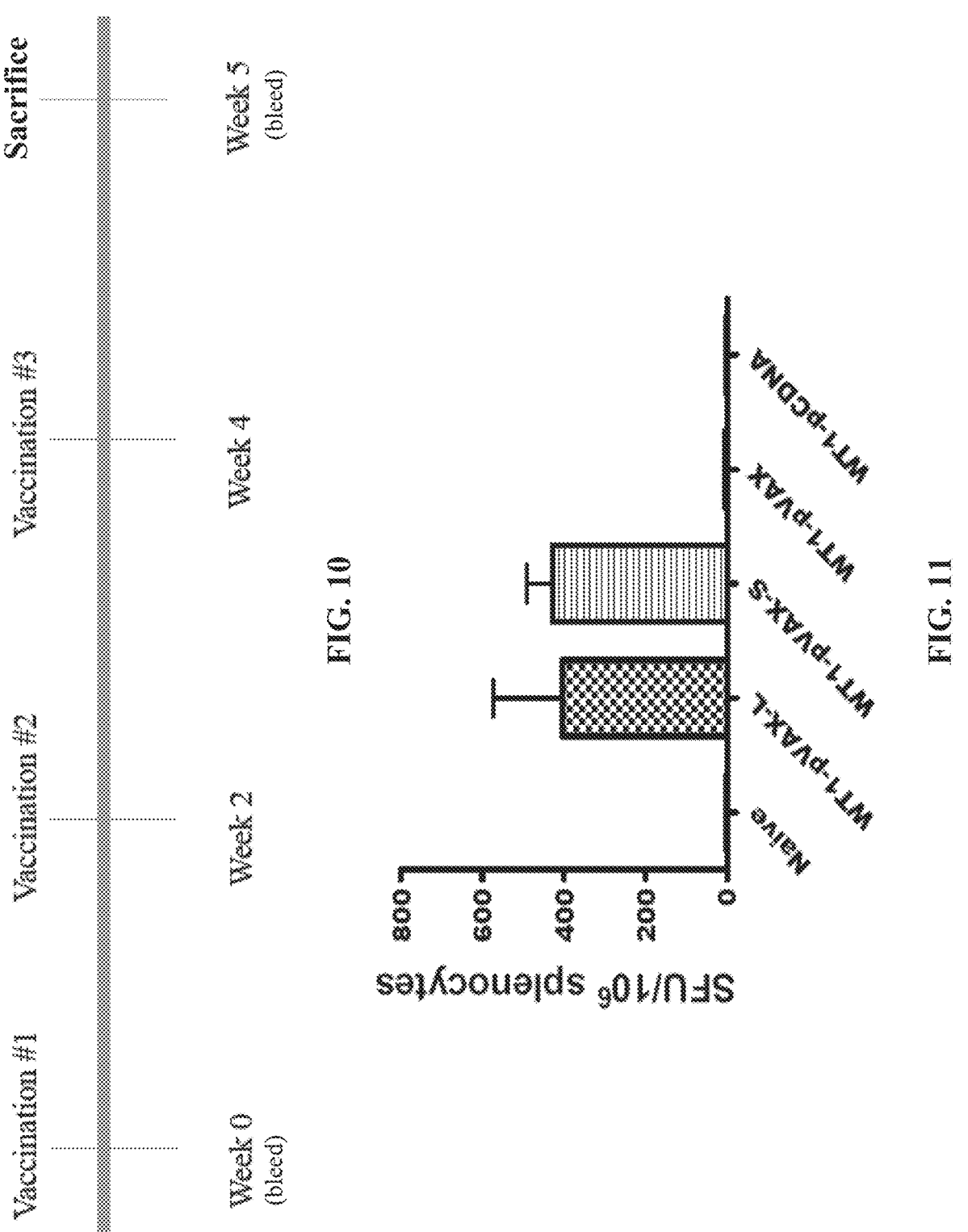
FIG. 10 shows a schematic illustrating an immunization regimen.
FIG. 11 shows a graph plotting immunization group vs. SFU per $10^6$ splenocytes.

Specifically, the immunization regimen included vaccination of each group of mice with 25 μg of the respective vaccine at week 0, week 2, week 3, and week 5 (FIG. 10). A bleed was taken from each mouse before vaccination at week 0, and thus, this bleed at week 0 served as a control for antibody induction. A second bleed was taken at week 5 when the mice were sacrificed. Splenocytes were also isolated from the sacrificed mice and used in the ELISpot assay described below to examine the T cell response.

Figure 12:
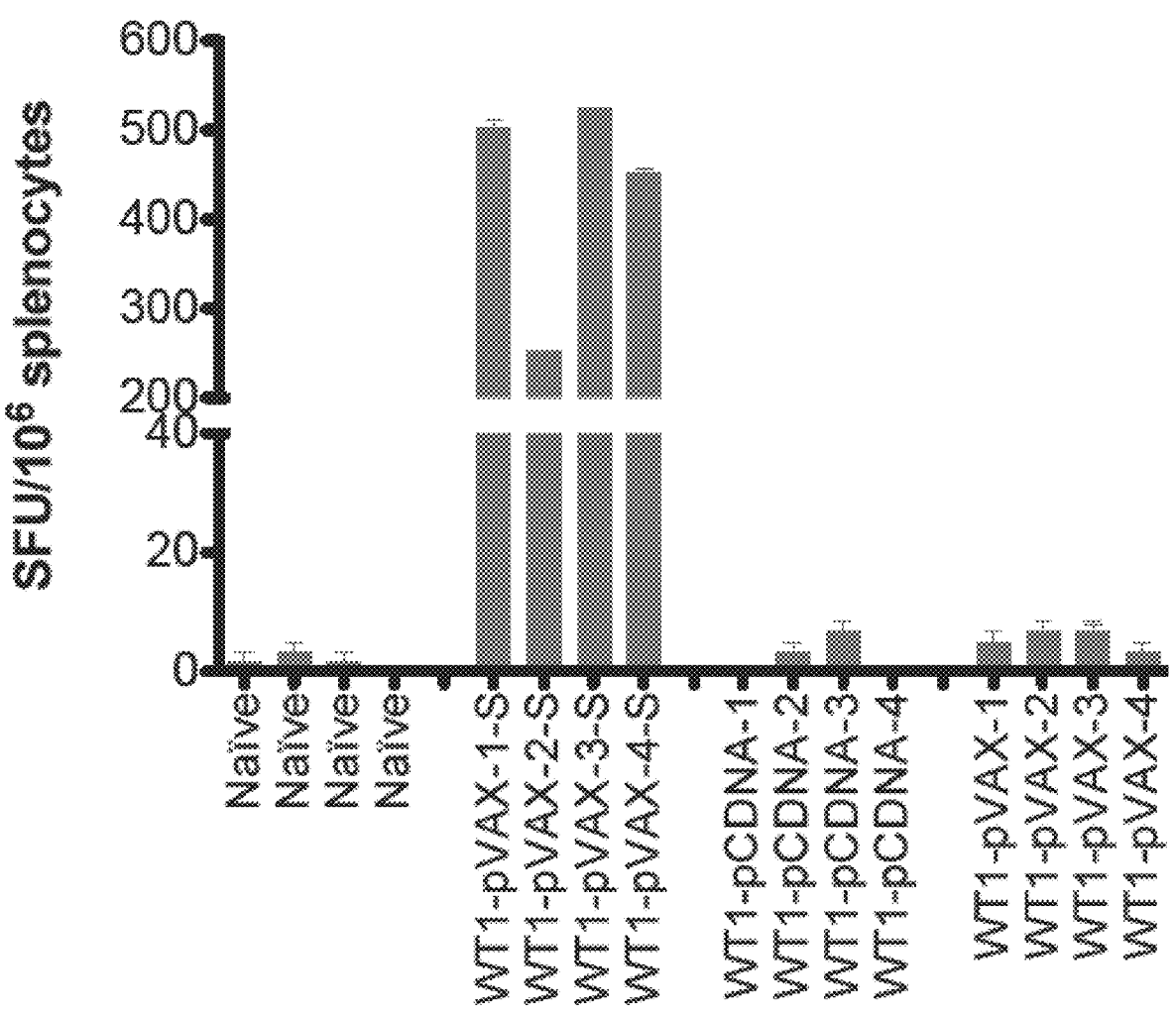
FIG. 12 shows a graph plotting immunization group vs. SFU per $10^6$ splenocytes.

The cellular immune response (i.e., T cell response) to ConWT1-L and ConWT1-S was examined using an ELISpot assay, in which interferon-gamma (IFN-γ) production by T cells was measured. As shown in FIGS. 11 and 12, immunization with the WT1-pVAX and WT1-pCDNA constructs yielded a similar T cell response as was observed in naïve mice. In contrast, the WT1-pVAX-L and WT1-pVAX-S constructs, which express ConWT1-L and ConWT-S, respectively, yielded significantly higher T cell responses as compared to the optimized and non-optimized constructs (i.e., WT1-pVAX and WT1-pCDNA, respectively). In FIGS. 11 and 12, error bars reflected the standard error of the mean (SEM).

In particular, the ConWT1-L and ConWT-S antigens induced a T cell response that was about 400-fold higher than the T cell response induced by the optimized and non-optimized constructs. Accordingly, these data indicated that modification and removal of the zinc fingers in WT1 significantly increased the immunogenicity of the WT1 immunogen, thereby providing a significant T cell response directed to the WT1 immunogen.

Figure 13:
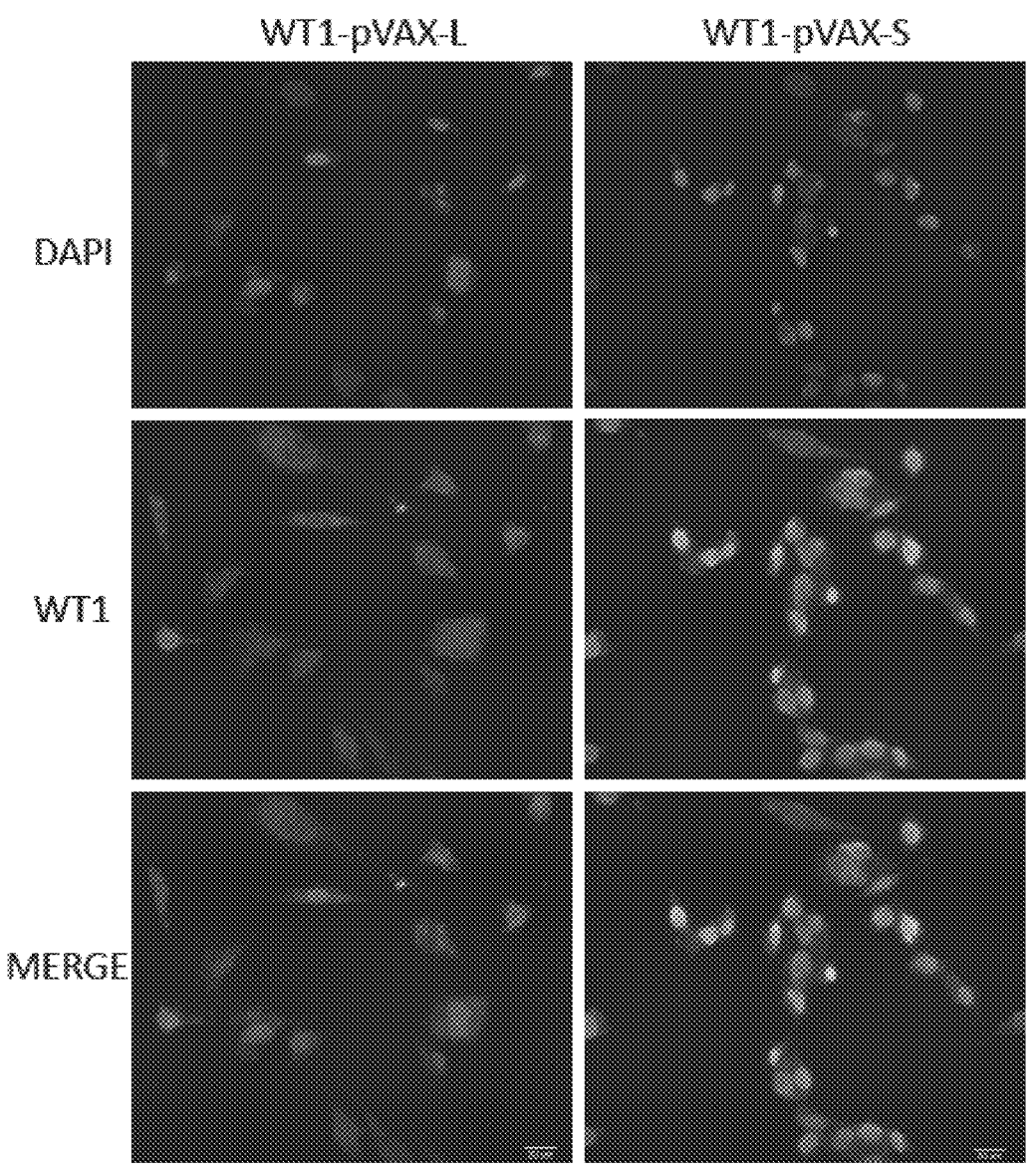
FIG. 13 shows staining of transfected cells.

The humoral immune response to the ConWT1-L and ConWT1-S antigens was examined by determining if sera from the week 5 bleed contained antibodies specific for the antigens. In particular, 293T cells were transfected with the vectors WT1-pVAX-L and WT1-pVAX-S. After transfection, the cells transfected with WT1-pVAX-L or WT1-pVAX-S were stained with DAPI to mark nucleic and sera from the week 5 bleed of mice immunized with WT1-pVAX-L or WT-pVAX-S. As shown in FIG. 13, the sera from mice immunized with WT1-pVAX-L or WT1-pVAX-S detected the ConWT1-L or ConWT1-S antigen, respectively, in the transfected cells. Accordingly, these data indicated that immunization with constructs expressing the ConWT1-L and ConWT1-S antigens resulted in production of antibodies that are immunoreactive with the ConWT1-L and ConWT1-S antigens.

Figure 14:
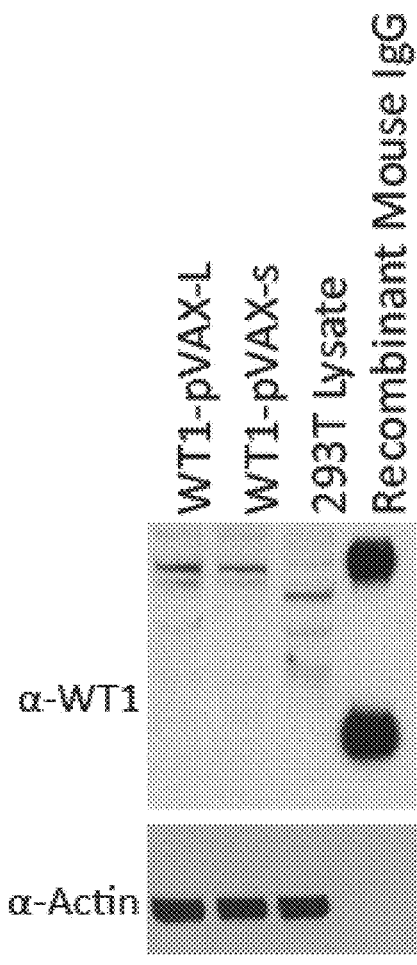
FIG. 14 shows an immunoblot.

Induction of the humoral immune response by the constructs expressing ConWT1-L and ConWT1-S was further examined by immunoblotting. In particular, lysates were obtained from the above transfected cells and were probed with the sera from mice immunized with WT1-pVAX-L or WT1-pVAX-S. FIG. 14 shows a representative immunoblot, in which lysate obtained from untransfected 293T cells served as a control for background. The immunoblot in FIG. 14 was also probed with an anti-actin antibody, which demonstrated that equivalent amounts of lysate were loaded between the three lanes. These data indicated that sera from the immunized mice contained antibodies that were immunoreactive with the ConWT1-L and ConWT1-S antigens, further confirming the cell staining results described above.

In summary, a construct expressing either the ConWT1-L or ConWT1-S antigen induced a significant T cell response that produced IFN-γ and antibodies that are immunoreactive with the ConWT1-S and ConWT-L antigens.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

The invention claimed is:

1. An isolated nucleic acid molecule comprising one or more nucleic acid sequences selected from the group consisting of: SEQ ID NO: 1 without the leader sequence, a fragment comprising at least 90% of the entire length of SEQ ID NO:1 without the leader sequence, a nucleic acid sequence that is at least 98% identical to SEQ ID NO: 1 over the entire length of SEQ ID NO: 1 without the leader sequence, a fragment comprising at least 90% of the entire length of a nucleic acid sequence that is at least 98% identical to SEQ ID NO: 1 over the entire length of SEQ ID NO:1 without the leader sequence, SEQ ID NO: 3 without the leader sequence, a fragment comprising at least 90% of the entire length of SEQ ID NO:3 without the leader sequence, a nucleic acid sequence that is at least 98% identical to SEQ ID NO:3 over the entire length of SEQ ID NO:3 without the leader sequence, and a fragment comprising at least 90% of the entire length of a nucleic acid sequence that is at least 98% identical to SEQ ID NO:3 over the entire length of SEQ ID NO:3 without the leader sequence.

2. The isolated nucleic acid molecule of claim 1, wherein the isolated nucleic molecule is incorporated into a plasmid or a viral vector.

3. The isolated nucleic acid molecule of claim 1, wherein the nucleic acid sequences encodes a protein or a fragment thereof comprising an amino acid sequence selected from the group consisting of: SEQ ID NO:2 without the leader sequence, a fragment comprising at least 90% of the entire length of SEQ ID NO:2 without the leader sequence, an amino acid sequence that is at least 98% identical to SEQ ID NO:2 over the entire length of SEQ ID NO: 2 without the leader sequence, a fragment comprising at least 90% of the entire length of an amino acid sequence that is at least 98% identical to SEQ ID NO:2 over the entire length of SEQ ID NO: 2 without the leader sequence, SEQ ID NO:4 without the leader sequence, a fragment comprising at least 90% of the entire length of SEQ ID NO:4 without the leader sequence, an amino acid sequence that is at least 98% identical to SEQ ID NO:4 over the entire length of SEQ ID NO: 4 without the leader sequence, and a fragment comprising at least 90% of the entire length of an amino acid sequence that is at least 98% identical to SEQ ID NO: 4 over the entire length of SEQ ID NO: 4 without the leader sequence.

4. A composition comprising the isolated nucleic acid molecule of claim 1.

5. A vaccine comprising the isolated nucleic acid molecule of claim 1.

6. The vaccine of claim 5, wherein the isolated nucleic acid molecule is incorporated into an expression vector.

7. The vaccine of claim 5, further comprising a pharmaceutically acceptable excipient.

8. The vaccine of claim 5, further comprising an adjuvant.

9. The vaccine of claim 5, further comprising an amino acid sequence selected from the group consisting of: SEQ ID NO:2 without the leader sequence, a fragment comprising at least 90% of the entire length of SEQ ID NO:2 without the leader sequence, an amino acid sequence that is at least 98% identical to SEQ ID NO:2 over the entire length of SEQ ID NO: 2 without the leader sequence, a fragment comprising at least 90% of the entire length of an amino acid sequence that is at least 98% identical to SEQ ID NO:2 over the entire length of SEQ ID NO: 2 without the leader sequence, SEQ ID NO:4 without the leader sequence, a fragment comprising at least 90% of the entire length of SEQ ID NO:4 over the entire length of SEQ ID NO: 4 without the leader sequence, an amino acid sequence that is at least 98% identical to SEQ ID NO:4 over the entire length of SEQ ID NO: 4 without the leader sequence, and a fragment comprising at least 90% of the entire length of an amino acid sequence that is at least 98% identical to SEQ ID NO:4 over the entire length of SEQ ID NO: 4 without the leader sequence.

10. The vaccine of claim 9, wherein the one or more nucleic acids are incorporated into an expression vector.

11. The vaccine of claim 9, further comprising a pharmaceutically acceptable excipient.

12. The vaccine of claim 9, further comprising an adjuvant.

13. A method of treating an individual who has a WT1-expressing tumor or preventing development of a WT1-expressing tumor in an individual comprising administering an amount of the vaccine of claim 5 effective to slow growth of, reduce, or eliminate WT1-expressing tumors.

14. A method of treating an individual who has a WT1-expressing tumor or preventing development of a WT1-expressing tumor comprising administering an amount of the vaccine of claim 9 effective to slow growth of, reduce, or eliminate WT1-expressing tumors.

15. A method of treating an individual who has a WT1-expressing tumor or preventing development of a WT1-expressing tumor comprising administering an amount of a vaccine effective to slow growth of, reduce, or eliminate WT1-expressing tumors, wherein the vaccine comprises a nucleic acid molecule comprising one or more nucleic acid sequences encoding a protein or a fragment thereof, wherein the protein comprises an amino acid sequence selected from the group consisting of: SEQ ID NO:2 without the leader sequence, a fragment comprising at least 90% of the entire length of SEQ ID NO: 2 without the leader sequence, an amino acid sequence that is at least 98% identical to SEQ ID NO:2 over the entire length of SEQ ID NO: 2 without the leader sequence, a fragment comprising at least 90% of the entire length of an amino acid sequence that is at least 98% identical to SEQ ID NO:2 over the entire length of SEQ ID NO: 2 without the leader sequence, SEQ ID NO:4 without the leader sequence, a fragment comprising at least 90% of the entire length of SEQ ID NO:4 without the leader sequence, an amino acid sequence that is at least 98% identical to SEQ ID NO: 4 over the entire length of SEQ ID NO: 4 without the leader sequence, and a fragment comprising at least 90% of the entire length of an amino acid sequence that is at least 98% identical to SEQ ID NO:4 over the entire length of SEQ ID NO: 4 without the leader sequence.

16. The method of claim 15, wherein the protein comprises the amino acid sequence as set forth in SEQ ID NO:2 without the leader sequence.

17. A method of treating an individual who has a WT1-expressing tumor or preventing development of a WT1-expressing tumor comprising administering an amount of a vaccine effective to slow growth of, reduce, or eliminate WT1-expressing tumors, wherein the vaccine comprises a protein comprising an amino acid sequence selected from the group consisting of: SEQ ID NO:2 without the leader sequence, a fragment comprising at least 90% of the entire length of SEQ ID NO:2 without the leader sequence, an amino acid sequence that is at least 98% identical to SEQ ID NO:2 over the entire length of SEQ ID NO: 2 without the leader sequence, a fragment comprising at least 90% of the entire length of an amino acid sequence that is at least 98% identical to SEQ ID NO:2 over the entire length of SEQ ID NO: 2 without the leader sequence, SEQ ID NO: 4 without the leader sequence, a fragment comprising at least 90% of the entire length of SEQ ID NO:4 without the leader sequence, an amino acid sequence that is at least 98% identical to SEQ ID NO:4 over the entire length of SEQ ID NO: 4 without the leader sequence, and a fragment comprising at least 90% of the entire length of an amino acid sequence that is at least 98% identical to SEQ ID NO:4 over the entire length of SEQ ID NO: 4 without the leader sequence.

18. The method of claim 17, wherein the protein comprises the amino acid sequence as set forth in SEQ ID NO:2 without the leader sequence.

* * * * *

```
                                    SEQUENCE LISTING

Sequence total quantity: 5
SEQ ID NO: 1            moltype = DNA   length = 1332
FEATURE                Location/Qualifiers
misc_feature           1..1332
                       note = Con WT1-L with modified Zinc Fingers nucleic acid
                        sequence
source                 1..1332
                       mol_type = other DNA
                       organism = synthetic construct SEQUENCE: 1
ggatccgcca ccatggactg gacctggatt ctgttcctgg tcgccgccgc aacacgggtg   60
catagtggga gtgatgtgag agacctgaac gccctgctgc cagcagtgcc atccctgcct  120
ggcgggggag gctgcgctct gccagtctct ggagcagctc agtgggctcc cgtgctggac  180
tttgcacccc ctgcagcccc ttacggaagt ctgggcggcc cacactcatt catcaaacag  240
gagccaagct ggggcggggc agatcctcat gaggaacagt gcctgtcagc cttcacagtc  300
cactttagcg ggcagttcac tggaaccgca ggagcttgta gatacggacc ctttggagca  360
ccaccccctt cccaggcacc ttctggacag gcacgcatgt tcccaaacgc tccctatctg  420
cctaattgtc tggaaagcca gcccgctatt aggaaccagg gctactccac agtggcattt  480
gacgggactc ctagctatgg acatacccca tcccaccatg ctgcacagtt tcctaatcac  540
tccttcaagc atgaggaccc catgggacag caggggtccc tgggagaaca gcagtactct  600
gtgcccctc ccgtgtacgg atgccacaca ccaactgaca gttgtacagg ctcacaggcc  660
ctgctgctgc gaactccata caacagtgat aatctgtatc agatgacctc acagctggag  720
tgcatgacat ggaaccagat gaatctgggc agcacactga aaggccatgc cactgggtac  780
gaatctgaca accacaccac acctatgctg tacagttgtg gagcccagta tagaatccac  840
actcatggag tcttcagagg cattcaggat gtgcggaag tcccaggagt ggcaccaact  900
atcgtgcgga gcgcctccga gaccaacgaa aagcgcccct ttatgggcgc ctaccctgga  960
ggcaataagc ggtatttcaa actgtctcac ctgcagatgg ggagtagaaa ggggaccgga 1020
gagaaacctt atcaggcgca ctttaaagat ggggaaaggc gcttctctcg cagtgaccag 1080
ctgaagcgag gacagcgacg aggaaccggg gtgaagccat ttcagtgcaa aacatgtcag 1140
agaaagttct caaggagcga tcacctgaag acccatacaa gaactcacac cggcaagacc 1200
agcgagaaac cattttcctg ccgatggccc tcttgtcaga gaaattcgc ccgctccgac 1260
gaactggtcc gacaccacaa tatgcatcag agaaatatga caaaactgca gctggctctg 1320
tgataactcg ag                                                      1332

SEQ ID NO: 2            moltype = AA   length = 436
FEATURE                Location/Qualifiers
REGION                 1..436
                       note = Con WT1-L with modified Zinc Fingers protein sequence
source                 1..436
                       mol_type = protein
                       organism = synthetic construct SEQUENCE: 2
MDWTWILFLV AAATRVHSGS DVRDLNALLP AVPSLPGGGG CALPVSGAAQ WAPVLDFAPP   60
AAPYGSLGGP HSFIKQEPSW GGADPHEEQC LSAFTVHFSG QFTGTAGACR YGPFGAPPPS  120
QAPSGQARMF PNAPYLPNCL ESQPAIRNQG YSTVAFDGTP SYGHTPSHHA AQFPNHSFKH  180
EDPMGQQGSL GEQQYSVPPP VYGCHTPTDS CTGSQALLLR TPYNSDNLYQ MTSQLECMTW  240
NQMNLGSTLK GHATGYESDN HTTPMLYSCG AQYRIHTHGV FRGIQDVRRV PGVAPTIVRS  300
ASETNEKRPF MGAYPGGNKR YFKLSHLQMG SRKGTGEKPY QGDFKDGERR FSRSDQLKRG  360
QRRGTGVKPF QCKTCQRKFS RSDHLKTHTR THTGKTSEKP FSCRWPSCQK KFARSDELVR  420
HHNMHQRNMT KLQLAL                                                   436

SEQ ID NO: 3            moltype = DNA   length = 954
FEATURE                Location/Qualifiers
misc_feature           1..954
                       note = Con WT1-S without Zinc fingers nucleic acid sequence
source                 1..954
                       mol_type = other DNA
                       organism = synthetic construct SEQUENCE: 3
ggatccgcca ccatggactg gacctggatt ctgtttctgg tggctgctgc tacacgggtg   60
cattctggga gcgatgtgag agacctgaac gccctgctgc cagctgtgcc aagtctgcct  120
ggcggggggag gctgcgcact gccagtgagc ggagcagctc agtgggctcc cgtcctggac  180
tttgcacccc ctgcagcacc ttacggctca ctgggcggcc cacacagctt catcaagcag  240
gagccatctt ggggcggggc cgatcctcac gaggaacagt gcctgagtgc tttcacagtc  300
cattttttcag gccagttcac tggaaccgca ggagcttgtc gatacggacc ctttggagcc  360
ccacccccta gccaggcacc ttccggacag gccagaatgt tcccaaacgc tccctatctg  420
cctaattgtc tggaatcaca gcctgcaatt cggaaccagg gctacagcac cgtcgccttt  480
gacgggcacc catcctatgg acacactccc tctcaccatg ctgcacagtt tcctaatcac  540
agcttcaagc atgaggaccc catgggacag caggggagcc tgggagaaca gcagtactcc  600
gtgccacccc ctgtctatgg ctgccataca ccaactgact cttgtacagg gagtcaggcc  660
ctgctgctgc gaactccata caactctgat aatctgtatc agatgacctg tcagctggag  720
tgcatgacct ggaaccagat gaatctgggc tccaccctga aaggccacgc cacagggtat  780
gaatccgaca accataccac acccatgctg tactcttgtg gcgcccagta tagaatccac  840
acccatggag tgttccgcgg cattcaggat gtgcggagag tcccaggagt cgctcccacc  900
atcgtgagat ccgccagtga gaccaatgaa aagagaccct ctgataact cgag          954
```

-continued

```
SEQ ID NO: 4              moltype = AA  length = 310
FEATURE                   Location/Qualifiers
REGION                    1..310
                          note = Con WT1-S without Zinc fingers protein sequence
source                    1..310
                          mol_type = protein
                          organism = synthetic construct
SEQUENCE: 4
MDWTWILFLV AAATRVHSGS DVRDLNALLP AVPSLPGGGG CALPVSGAAQ WAPVLDFAPP  60
AAPYGSLGGP HSFIKQEPSW GGADPHEEQC LSAFTVHFSG QFTGTAGACR YGPFGAPPPS  120
QAPSGQARMF PNAPYLPNCL ESQPAIRNQG YSTVAFDGTP SYGHTPSHHA AQFPNHSFKH  180
EDPMGQQGSL GEQQYSVPPP VYGCHTPTDS CTGSQALLLR TPYNSDNLYQ MTSQLECMTW  240
NQMNLGSTLK GHATGYESDN HTTPMLYSCG AQYRIHTHGV FRGIQDVRRV PGVAPTIVRS  300
ASETNEKRPF                                                        310

SEQ ID NO: 5              moltype = AA  length = 419
FEATURE                   Location/Qualifiers
REGION                    1..419
                          note = Con WT1 protein sequence
source                    1..419
                          mol_type = protein
                          organism = synthetic construct
SEQUENCE: 5
MGSDVRDLNA LLPAVPSLPG GGGCALPVSG AAQWAPVLDF APPAAPYGSL GGPHSFIKQE  60
PSWGGADPHE EQCLSAFTVH FSGQFTGTAG ACRYGPFGAP PPSQAPSGQA RMFPNAPYLP  120
NCLESQPAIR NQGYSTVAFD GTPSYGHTPS HHAAQFPNHS FKHEDPMGQQ GSLGEQQYSV  180
PPPVYGCHTP TDSCTGSQAL LLRTPYNSDN LYQMTSQLEC MTWNQMNLGS TLKGHATGYE  240
SDNHTTPMLY SCGAQYRIHT HGVFRGIQDV RRVPGVAPTI VRSASETNEK RPFMCAYPGC  300
NKRYFKLSHL QMHSRKHTGE KPYQCDFKDC ERRFSRSDQL KRHQRRHTGV KPFQCKTCQR  360
KFSRSDHLKT HTRTHTGKTS EKPFSCRWPS CQKKFARSDE LVRHHNMHQR NMTKLQLAL   419
```